US012076035B2

(12) United States Patent
Martin et al.

(10) Patent No.: US 12,076,035 B2
(45) Date of Patent: Sep. 3, 2024

(54) ARTICULATING RETRIEVAL DEVICES

(71) Applicant: Covidien LP, Mansfield, MA (US)

(72) Inventors: Brian B. Martin, Felton, CA (US);
Martin S. Dieck, Campbell, CA (US)

(73) Assignee: Covidien LP, Mansfield, MA (US)

( * ) Notice: Subject to any disclaimer, the term of this patent is extended or adjusted under 35 U.S.C. 154(b) by 289 days.

(21) Appl. No.: 17/454,424

(22) Filed: Nov. 10, 2021

(65) Prior Publication Data
US 2022/0061865 A1    Mar. 3, 2022

Related U.S. Application Data

(63) Continuation of application No. 16/120,155, filed on Aug. 31, 2018, now Pat. No. 11,202,646, which is a continuation of application No. 11/852,975, filed on Sep. 10, 2007, now Pat. No. 10,064,635, which is a continuation-in-part of application No. 11/736,537, filed on Apr. 17, 2007, now Pat. No. 8,512,352.

(51) Int. Cl.
*A61B 17/221* (2006.01)
(52) U.S. Cl.
CPC .... *A61B 17/221* (2013.01); *A61B 2017/2212* (2013.01); *A61B 2017/2215* (2013.01)
(58) Field of Classification Search
CPC .......... A61B 17/221; A61B 2014/2212; A61B 2014/2215
See application file for complete search history.

(56) References Cited

U.S. PATENT DOCUMENTS

| | | |
|---|---|---|
| 2,918,919 A | 12/1959 | Wallace |
| 2,943,626 A | 7/1960 | Enrico |
| 3,996,938 A | 12/1976 | Clark |
| 4,347,846 A | 9/1982 | Dormia |
| 4,611,594 A | 9/1986 | Grayhack et al. |
| 4,699,147 A | 10/1987 | Chilson et al. |
| 4,790,812 A | 12/1988 | Hawkins et al. |
| 4,807,626 A | 2/1989 | Mcgirr |
| 4,832,055 A | 5/1989 | Palestrant |
| 4,873,978 A | 10/1989 | Ginsburg |
| 4,969,891 A | 11/1990 | Gewertz |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A | 3/1993 | Phan et al. |
| 5,300,086 A | 4/1994 | Gory et al. |
| 5,443,478 A | 8/1995 | Purdy |

(Continued)

FOREIGN PATENT DOCUMENTS

| | | |
|---|---|---|
| CN | 1640505 | 7/2005 |
| DE | 3501707 A1 | 7/1986 |

(Continued)

*Primary Examiner* — Sarah A Long
(74) *Attorney, Agent, or Firm* — Fortem IP LLP

(57) ABSTRACT

The devices and methods described herein relate to improved structures for removing obstructions from body lumens. Such devices have applicability in through-out the body, including clearing of blockages within the vasculature, by addressing the frictional resistance on the obstruction prior to attempting to translate and/or mobilize the obstruction within the body lumen.

21 Claims, 17 Drawing Sheets

(56) References Cited

U.S. PATENT DOCUMENTS

| | | |
|---|---|---|
| 5,458,375 A | 10/1995 | Anspach et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 6,001,118 A | 12/1999 | Daniel et al. |
| 6,033,394 A | 3/2000 | Mdlund et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,159,220 A | 12/2000 | Gobron et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,190,394 B1 | 2/2001 | Lind et al. |
| 6,217,609 B1 | 4/2001 | Haverkost |
| 6,221,006 B1 | 4/2001 | Dubrul et al. |
| 6,245,089 B1 | 6/2001 | Daniel et al. |
| 6,248,113 B1 | 6/2001 | Fina |
| 6,264,664 B1 | 7/2001 | Avellanet |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 * | 10/2002 | Palmer ............... A61B 17/221 606/113 |
| 6,485,497 B2 | 11/2002 | Wensel et al. |
| 6,494,884 B2 | 12/2002 | Gifford et al. |
| 6,506,204 B2 | 1/2003 | Mazzocchi |
| 6,511,492 B1 * | 1/2003 | Rosenbluth ...... A61B 17/22032 606/159 |
| 6,514,273 B1 | 2/2003 | Voss et al. |
| 6,530,935 B2 | 3/2003 | Wensel et al. |
| 6,540,657 B2 | 4/2003 | Cross et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,534,252 B2 | 5/2009 | Sepetka et al. |
| 8,105,333 B2 | 1/2012 | Sepetka et al. |
| 8,603,014 B2 | 12/2013 | Alleman et al. |
| 8,837,800 B1 | 9/2014 | Bammer et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2001/0041909 A1 | 11/2001 | Tsugita et al. |
| 2001/0044634 A1 | 11/2001 | Don et al. |
| 2001/0051810 A1 | 12/2001 | Dubrul et al. |
| 2002/0002396 A1 | 1/2002 | Fulkerson |
| 2002/0004667 A1 | 1/2002 | Adams et al. |
| 2002/0026211 A1 | 2/2002 | Khosravi et al. |
| 2002/0058904 A1 | 5/2002 | Boock et al. |
| 2002/0062135 A1 | 5/2002 | Mazzocchi et al. |
| 2002/0072764 A1 | 6/2002 | Sepetka et al. |
| 2002/0082558 A1 | 6/2002 | Samson et al. |
| 2002/0123765 A1 | 9/2002 | Sepetka et al. |
| 2002/0128680 A1 * | 9/2002 | Pavlovic ............... A61F 2/01 606/200 |
| 2002/0151928 A1 | 10/2002 | Leslie et al. |
| 2002/0169474 A1 | 11/2002 | Kusleika et al. |

(56) References Cited

U.S. PATENT DOCUMENTS

| | | | |
|---|---|---|---|
| 2002/0173819 A1* | 11/2002 | Leeflang | A61F 2/014 606/200 |
| 2002/0188314 A1 | 12/2002 | Anderson et al. | |
| 2002/0193825 A1 | 12/2002 | Mcguckin et al. | |
| 2003/0004542 A1 | 1/2003 | Wensel et al. | |
| 2003/0023265 A1 | 1/2003 | Forber | |
| 2003/0040771 A1 | 2/2003 | Hyodoh et al. | |
| 2003/0050663 A1 | 3/2003 | Khachin et al. | |
| 2003/0060782 A1 | 3/2003 | Bose et al. | |
| 2003/0093087 A1 | 5/2003 | Jones et al. | |
| 2003/0144687 A1 | 7/2003 | Brady et al. | |
| 2003/0153935 A1 | 8/2003 | Mialhe | |
| 2003/0195556 A1 | 10/2003 | Stack et al. | |
| 2003/0195616 A1 | 10/2003 | Pinchasik et al. | |
| 2004/0068288 A1 | 4/2004 | Palmer et al. | |
| 2004/0073243 A1 | 4/2004 | Sepetka et al. | |
| 2004/0079429 A1 | 4/2004 | Miller et al. | |
| 2004/0133232 A1 | 7/2004 | Rosenbluth et al. | |
| 2004/0138692 A1 | 7/2004 | Phung et al. | |
| 2004/0153025 A1 | 8/2004 | Seifert et al. | |
| 2004/0153118 A1 | 8/2004 | Clubb et al. | |
| 2004/0172056 A1 | 9/2004 | Guterman et al. | |
| 2004/0199201 A1 | 10/2004 | Kellett et al. | |
| 2004/0199243 A1 | 10/2004 | Yodfat | |
| 2004/0210116 A1 | 10/2004 | Nakao | |
| 2004/0267301 A1 | 12/2004 | Boylan et al. | |
| 2005/0004594 A1 | 1/2005 | Nool et al. | |
| 2005/0033348 A1 | 2/2005 | Sepetka et al. | |
| 2005/0038447 A1 | 2/2005 | Huffmaster | |
| 2005/0043680 A1 | 2/2005 | Segal et al. | |
| 2005/0043756 A1 | 2/2005 | Lavelle et al. | |
| 2005/0049619 A1 | 3/2005 | Sepetka et al. | |
| 2005/0055033 A1 | 3/2005 | Leslie et al. | |
| 2005/0055047 A1 | 3/2005 | Greenhalgh | |
| 2005/0059995 A1 | 3/2005 | Sepetka et al. | |
| 2005/0080356 A1 | 4/2005 | Dapolito et al. | |
| 2005/0085826 A1 | 4/2005 | Nair et al. | |
| 2005/0085847 A1 | 4/2005 | Galdonik et al. | |
| 2005/0085849 A1 | 4/2005 | Sepetka et al. | |
| 2005/0090857 A1 | 4/2005 | Kusleika et al. | |
| 2005/0090858 A1 | 4/2005 | Pavlovic | |
| 2005/0125024 A1 | 6/2005 | Sepetka et al. | |
| 2005/0131450 A1 | 6/2005 | Nicholson et al. | |
| 2005/0171566 A1 | 8/2005 | Kanamaru | |
| 2005/0203571 A1 | 9/2005 | Mazzocchi et al. | |
| 2005/0209609 A1 | 9/2005 | Wallace | |
| 2005/0216030 A1 | 9/2005 | Sepetka et al. | |
| 2005/0216050 A1 | 9/2005 | Sepetka et al. | |
| 2005/0234501 A1 | 10/2005 | Barone | |
| 2005/0234505 A1 | 10/2005 | Diaz et al. | |
| 2005/0277978 A1 | 12/2005 | Greenhalgh | |
| 2005/0283166 A1 | 12/2005 | Greenhalgh | |
| 2005/0283186 A1 | 12/2005 | Berrada et al. | |
| 2006/0004404 A1 | 1/2006 | Khachin et al. | |
| 2006/0009784 A1 | 1/2006 | Behl et al. | |
| 2006/0047286 A1 | 3/2006 | West | |
| 2006/0058836 A1 | 3/2006 | Bose et al. | |
| 2006/0058837 A1* | 3/2006 | Bose | A61B 17/3207 606/200 |
| 2006/0058838 A1 | 3/2006 | Bose et al. | |
| 2006/0095070 A1 | 5/2006 | Gilson et al. | |
| 2006/0129166 A1 | 6/2006 | Lavelle | |
| 2006/0129180 A1 | 6/2006 | Tsugita et al. | |
| 2006/0155305 A1 | 7/2006 | Freudenthal et al. | |
| 2006/0190070 A1 | 8/2006 | Dieck et al. | |
| 2006/0195137 A1 | 8/2006 | Sepetka et al. | |
| 2006/0229638 A1 | 10/2006 | Abrams et al. | |
| 2006/0253145 A1 | 11/2006 | Lucas | |
| 2006/0276805 A1 | 12/2006 | Yu | |
| 2006/0282111 A1 | 12/2006 | Morsi | |
| 2007/0100372 A1 | 5/2007 | Schaeffer | |
| 2007/0112374 A1 | 5/2007 | Paul et al. | |
| 2007/0118165 A1 | 5/2007 | Demello et al. | |
| 2007/0185500 A1 | 8/2007 | Martin et al. | |
| 2007/0185501 A1 | 8/2007 | Martin et al. | |
| 2007/0197103 A1 | 8/2007 | Martin et al. | |
| 2007/0198029 A1 | 8/2007 | Martin et al. | |
| 2007/0198030 A1 | 8/2007 | Martin et al. | |
| 2007/0225749 A1 | 9/2007 | Martin et al. | |
| 2007/0265656 A1 | 11/2007 | Amplatz et al. | |
| 2008/0109031 A1 | 5/2008 | Sepetka et al. | |
| 2008/0183198 A1 | 7/2008 | Sepetka et al. | |
| 2008/0188885 A1 | 8/2008 | Sepetka et al. | |
| 2008/0262528 A1 | 10/2008 | Martin | |
| 2008/0262532 A1 | 10/2008 | Martin | |
| 2009/0192518 A1 | 7/2009 | Leanna et al. | |
| 2009/0287291 A1 | 11/2009 | Becking et al. | |
| 2009/0299393 A1 | 12/2009 | Martin et al. | |
| 2010/0076452 A1 | 3/2010 | Sepetka et al. | |
| 2010/0185210 A1 | 7/2010 | Hauser et al. | |
| 2011/0166586 A1 | 7/2011 | Sepetka et al. | |
| 2011/0288572 A1 | 11/2011 | Martin | |
| 2012/0143230 A1 | 6/2012 | Sepetka et al. | |
| 2012/0197285 A1 | 8/2012 | Martin et al. | |
| 2013/0030461 A1 | 1/2013 | Marks et al. | |
| 2013/0281788 A1 | 10/2013 | Garrison | |
| 2014/0276074 A1 | 9/2014 | Warner | |
| 2014/0343595 A1 | 11/2014 | Monstadt et al. | |
| 2015/0359547 A1 | 12/2015 | Vale et al. | |
| 2016/0015402 A1 | 1/2016 | Brady et al. | |
| 2016/0015935 A1 | 1/2016 | Chan et al. | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113665 A1 | 4/2016 | Brady et al. | |
| 2016/0151618 A1 | 6/2016 | Powers et al. | |
| 2016/0157985 A1 | 6/2016 | Vo et al. | |
| 2016/0199620 A1 | 7/2016 | Pokorney et al. | |
| 2016/0296690 A1 | 10/2016 | Kume et al. | |
| 2016/0302808 A1 | 10/2016 | Loganathan et al. | |
| 2016/0375180 A1 | 12/2016 | Anzai | |
| 2017/0079766 A1 | 3/2017 | Wang et al. | |
| 2017/0079767 A1 | 3/2017 | Leon-Yip | |
| 2017/0086862 A1 | 3/2017 | Vale et al. | |
| 2017/0100143 A1 | 4/2017 | Grandfield | |
| 2017/0105743 A1 | 4/2017 | Vale et al. | |
| 2017/0164963 A1 | 6/2017 | Goyal | |
| 2017/0215902 A1 | 8/2017 | Leynov et al. | |
| 2017/0224953 A1 | 8/2017 | Tran et al. | |
| 2017/0281909 A1 | 10/2017 | Northrop et al. | |
| 2017/0290599 A1 | 10/2017 | Youn et al. | |
| 2018/0049762 A1 | 2/2018 | Seip et al. | |
| 2018/0084982 A1 | 3/2018 | Yamashita et al. | |
| 2018/0116717 A1 | 5/2018 | Taff et al. | |
| 2018/0132876 A1 | 5/2018 | Zaidat | |
| 2018/0140314 A1 | 5/2018 | Goyal et al. | |
| 2018/0140315 A1 | 5/2018 | Bowman et al. | |
| 2018/0140354 A1 | 5/2018 | Lam et al. | |
| 2018/0185614 A1 | 7/2018 | Garrison et al. | |

FOREIGN PATENT DOCUMENTS

| | | |
|---|---|---|
| EP | 1312314 A1 | 5/2003 |
| EP | 2319575 B1 | 11/2013 |
| JP | 2002537943 A | 11/2002 |
| JP | 2007522881 A | 8/2007 |
| JP | 2007252951 A | 10/2007 |
| JP | 2008539958 A | 11/2008 |
| JP | 2014004219 A | 1/2014 |
| JP | 6249841 B2 | 12/2017 |
| JP | 2018118132 A | 8/2018 |
| KR | 20180102877 A | 9/2018 |
| WO | 9601591 A1 | 1/1996 |
| WO | 9609941 A1 | 4/1996 |
| WO | 9727808 A1 | 8/1997 |
| WO | 9727893 A1 | 8/1997 |
| WO | 9803120 A1 | 1/1998 |
| WO | 0053120 A1 | 9/2000 |
| WO | 0072909 A1 | 12/2000 |
| WO | 0132254 A1 | 5/2001 |
| WO | 0167967 A1 | 9/2001 |
| WO | 0202162 A2 | 1/2002 |
| WO | 0228291 A2 | 4/2002 |
| WO | 03000334 A1 | 1/2003 |

(56) References Cited

FOREIGN PATENT DOCUMENTS

| WO | 03061730 A2 | 7/2003 |
|---|---|---|
| WO | 03089039 A1 | 10/2003 |
| WO | 2006031410 A2 | 3/2006 |
| WO | 2006122076 A1 | 11/2006 |
| WO | 2007092820 A2 | 8/2007 |
| WO | 2008131116 A1 | 10/2008 |
| WO | 2009017827 A1 | 2/2009 |
| WO | 2009034456 A2 | 3/2009 |
| WO | 2009086482 A1 | 7/2009 |
| WO | 2010102307 A1 | 9/2010 |
| WO | 2011091383 A1 | 7/2011 |
| WO | 2011130579 A1 | 10/2011 |
| WO | 2012009675 A2 | 1/2012 |
| WO | 2012154782 A1 | 11/2012 |
| WO | 2012162437 A1 | 11/2012 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

\* cited by examiner

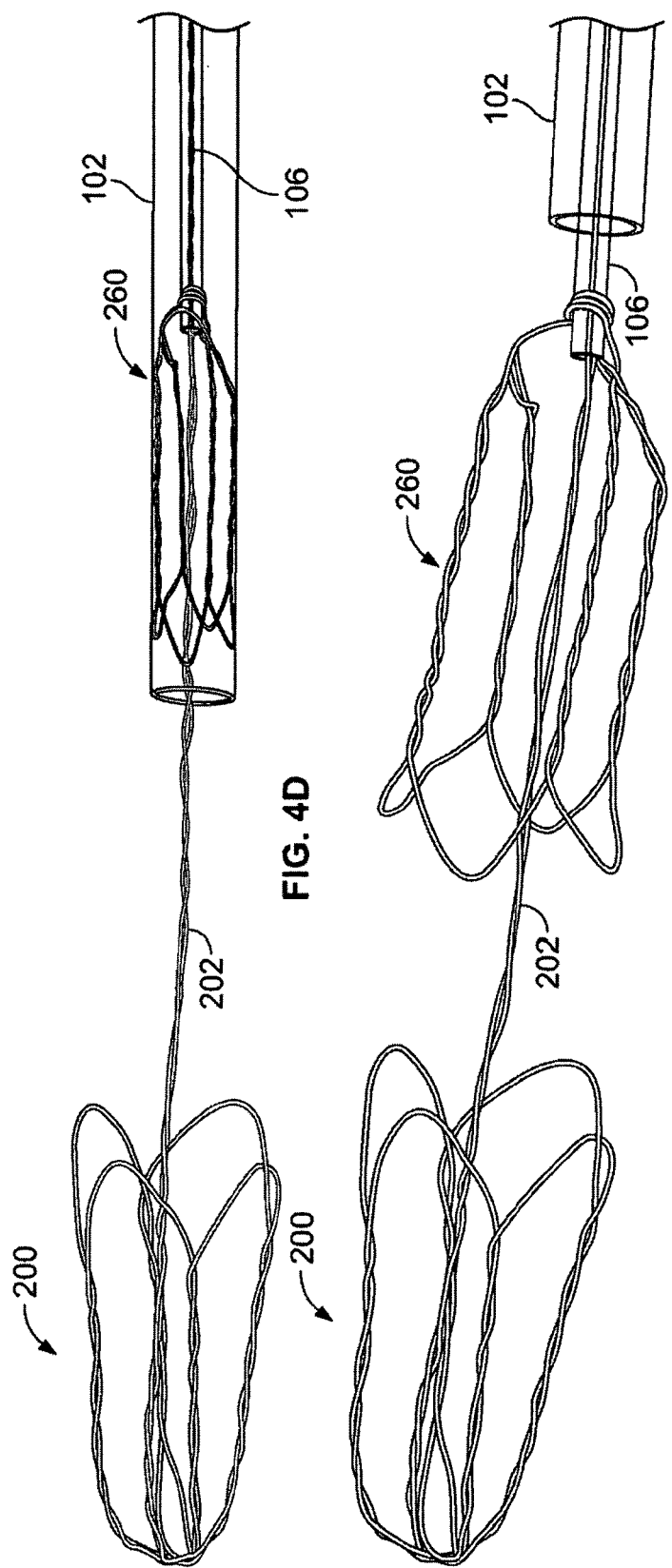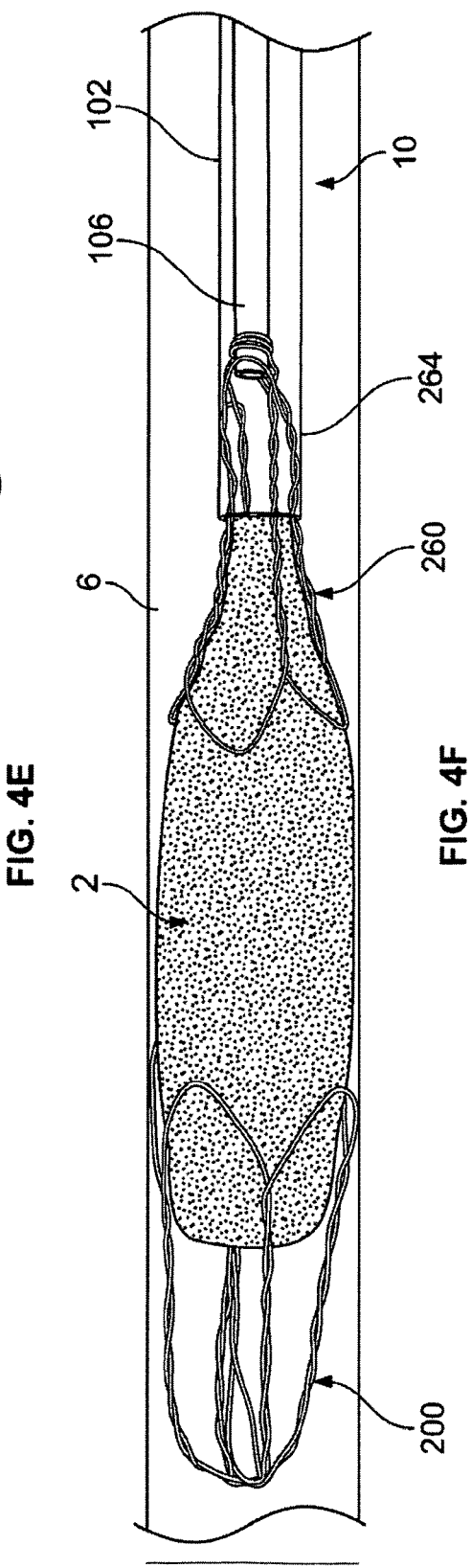

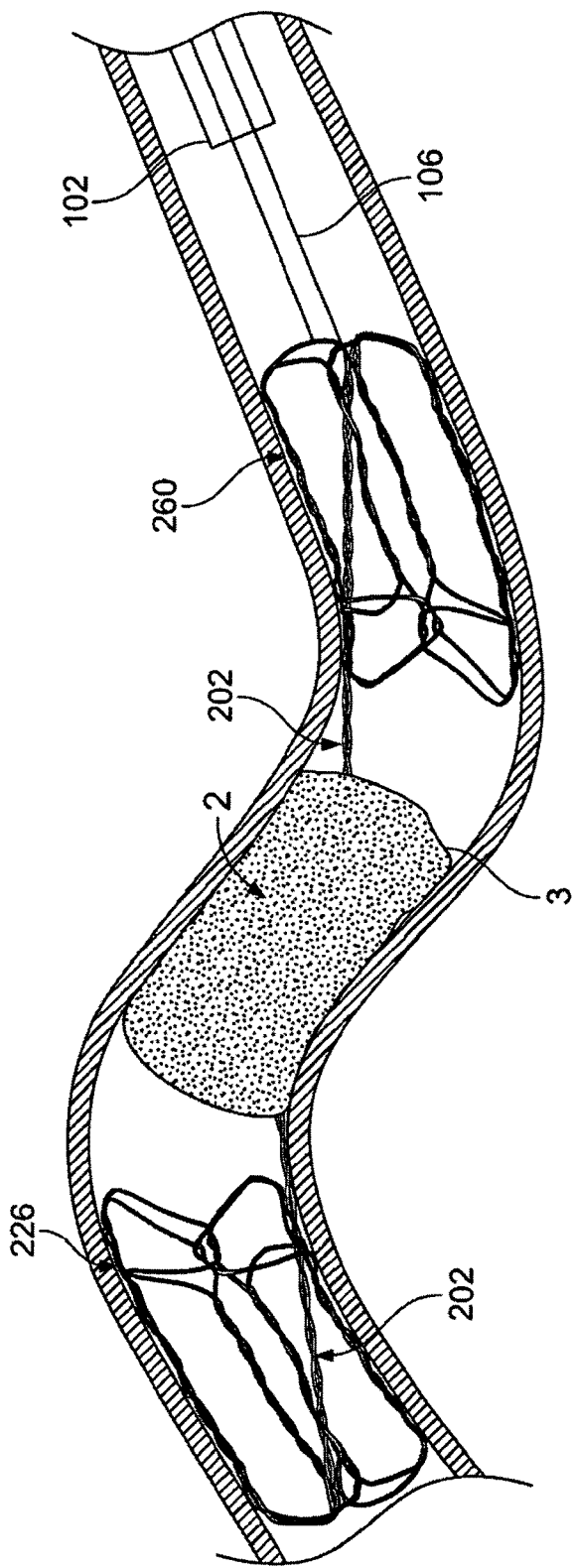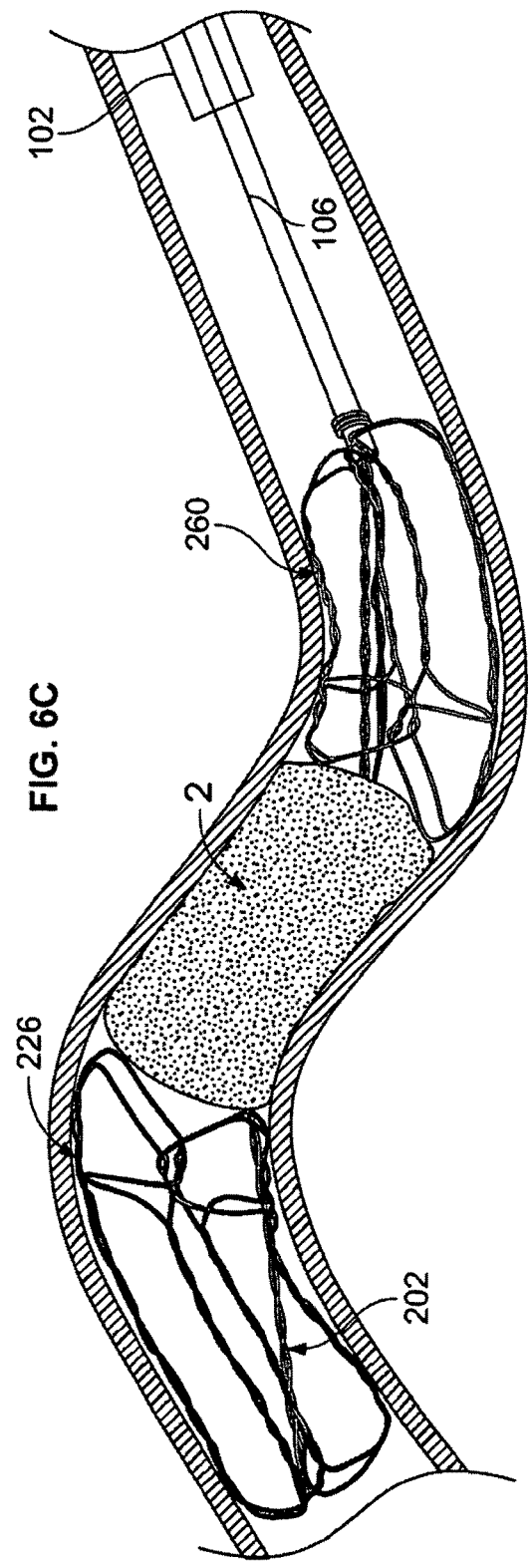

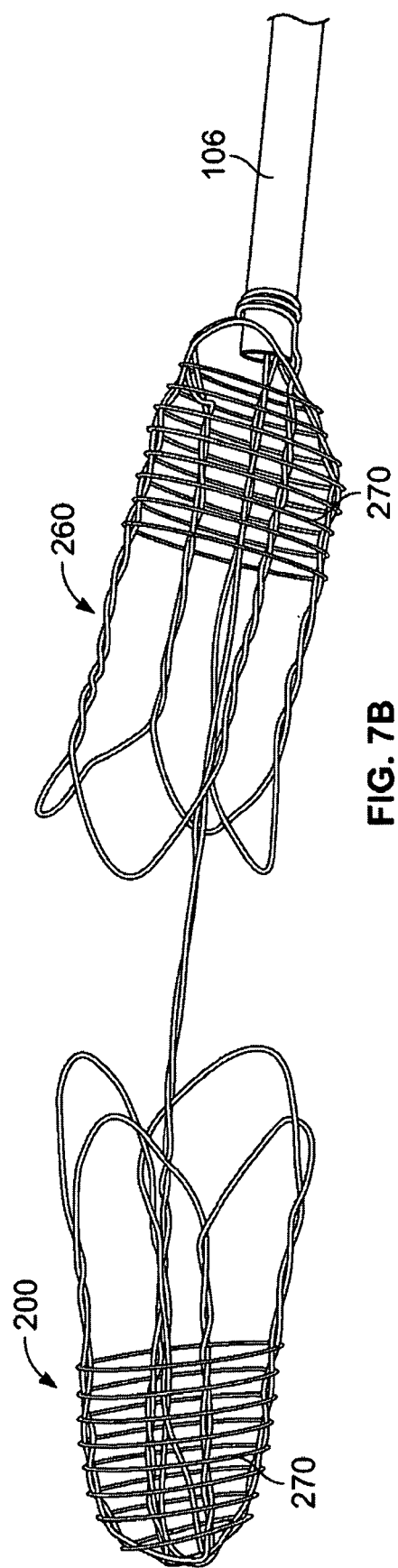
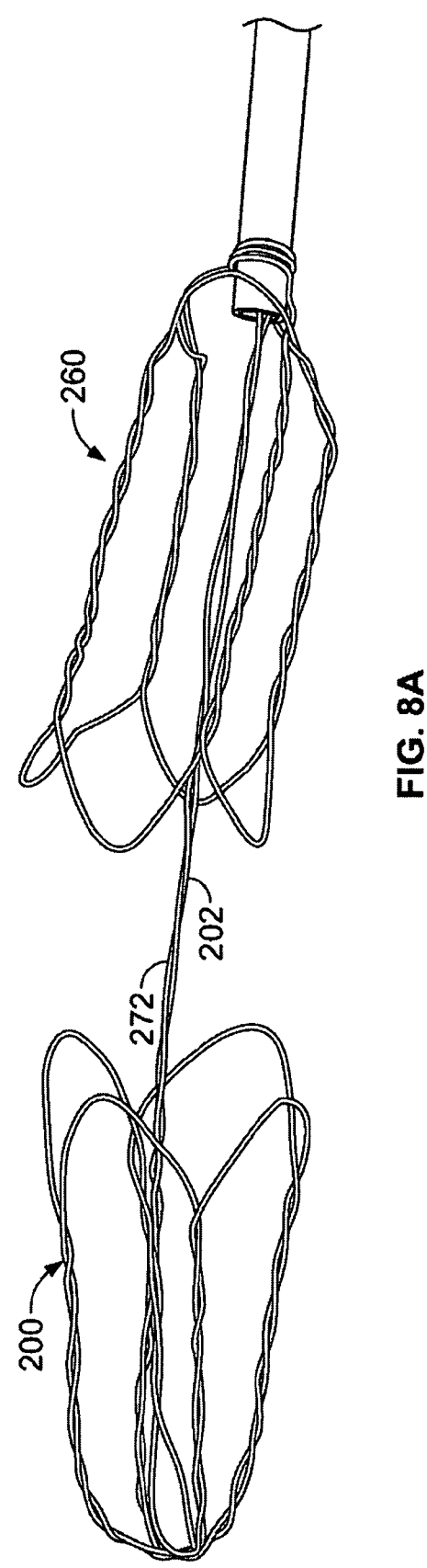

ARTICULATING RETRIEVAL DEVICES

CROSS-REFERENCE TO RELATED APPLICATION

The present application is a continuation of U.S. patent application Ser. No. 16/120,155, filed on Aug. 31, 2018; which is a continuation of U.S. patent application Ser. No. 11/852,975, filed on Sep. 10, 2007, now U.S. Pat. No. 10,064,635; which is a continuation-in-part of U.S. patent application Ser. No. 11/736,537, filed on Apr. 17, 2007, now U.S. Pat. No. 8,512,352; the disclosures of which are incorporated by reference herein in their entirety.

FIELD OF THE INVENTION

The devices described herein are constructed in wire form where the wires diverge from a main bundle to form a variety of shapes that form a composite device. The benefit of such a diverging wire construction is that the composite complex device can be of a "joint-less" construction. Such devices have applicability throughout the body, including clearing of blockages within body lumens, such as the vasculature, by providing a capturing portion that can envelop the obstruction to address the frictional resistance between the obstruction and body lumen prior to attempting to translate and/or mobilize the obstruction within the body lumen. In addition, the devices described below include features that prevent unwanted and premature mobilization of the obstruction when removing the obstruction through tortuous anatomy.

BACKGROUND OF THE INVENTION

Many medical device applications require advancement of device in a reduced profile to a remote site within the body, where on reaching a target site the device assumes or is deployed into a relatively larger profile. Applications in the cerebral vasculature are one such example of medical procedures where a catheter advances from a remote part of the body (typically a leg) through the vasculature and into the cerebral region of the vasculature to deploy a device. Accordingly, the deployed devices must be capable of achieving a larger profile while being able to fit within a small catheter or microcatheter. In addition, the degree to which a physician is limited in accessing remote regions of the cerebral vasculature is directly related to the limited ability of the device to constrain into a reduced profile for delivery.

Treatment of ischemic stroke is one such area where a need remains to deliver a device in a reduced profile and deploy the device to ultimately remove a blockage in an artery leading to the brain. Left untreated, the blockage causes a lack of supply of oxygen and nutrients to the brain tissue. The brain relies on its arteries to supply oxygenated blood from the heart and lungs. The blood returning from the brain carries carbon dioxide and cellular waste. Blockages that interfere with this supply eventually cause the brain tissue to stop functioning. If the disruption in supply occurs for a sufficient amount of time, the continued lack of nutrients and oxygen causes irreversible cell death (infarction). Accordingly, immediate medical treatment of an ischemic stroke is critical for the recovery of a patient.

Naturally, areas outside of ischemic stroke applications can also benefit from devices that can assume a profile for ultimate delivery to remote regions of the body.

Accordingly, a need remains for devices that can assume deployed configurations and are fabricated to eliminate or reduce the number of joints and/or connection points in the device. Elimination of the joints also allows the device to have a compact and smooth configuration making it easier for delivery through a microcatheter, and leads to a safer device less prone to breaking or embolizing. Another need remains for a device that can translate over and securely remove the obstruction from tortuous anatomy.

SUMMARY OF THE INVENTION

The examples discussed herein show the inventive device in a form that is suitable to retrieve obstructions or clots within the vasculature. The term obstructions may include blood clot, plaque, cholesterol, thrombus, naturally occurring foreign bodies (i.e., a part of the body that is lodged within the lumen), a non-naturally occurring foreign body (i.e., a portion of a medical device or other non-naturally occurring substance lodged within the lumen.) However, the devices are not limited to such applications and can apply to any number of medical applications where elimination or reduction of the number of connection points is desired.

In one variation of the devices described herein, the device comprises a main bundle or group of wires that diverge to form a device having various shapes but few or no connections points or joints (where fabrication of such a construction is referred to as "jointless"). Clearly, the inventive devices described herein are not limited to such a jointless construction. Additional variation includes one or more leading wires that are attached to a capturing portion as described below.

In one variation, the device includes a main bundle comprising one or a group of wires. The device also includes a capturing portion formed by the wires or wire of the main bundle. The capturing portion includes a cavity or space that is able to surround the obstruction. Accordingly, the capturing portion includes an open proximal end, a permeable distal end, and a capturing surface extending therebetween. The permeable distal end should be sufficiently permeable to allow blood to flow but have sufficient surface area to prevent escape of the obstruction or to prevent particles such as pieces of clot or emboli that would otherwise cause a complication if such pieces migrate through the body. In some variations of the device, the capturing portion is formed from the group of wires such that the group of wires diverges from the second end of the main bundle to form the permeable distal end, the group of wires extend back in a proximal direction to form the capturing surface and open proximal end about the main bundle, such that articulation of the capturing portion relative to the main bundle does not cause the open proximal end to reduce in size. Although some closing of the open proximal end can occur, it will not be sufficient to interfere with the obstruction as the capturing portion moves over the obstruction. In some variations, the permeable end may be the distal end or be towards the distal end (meaning anywhere past a proximal end). The terms distal and proximal are relative to the physician (e.g., the distal end is the farthest end from the catheter/physician).

The devices of the present invention typically include a main bundle from which the wires extend. In most case, the main bundle extends for a length sufficient to withdraw the device from a body of a patient. Accordingly, in such cases, the main bundle shall extend through the length of a catheter. In alternate constructions, the main bundle may be affixed to a single wire or member. In such cases, a main bundle does not extend from the capturing portion to the exterior of the patient. Instead, a single wire extends to the operator interface of the device where the wire is affixed to a main bundle.

Devices of the present invention can incorporate any number of wires of different characteristics including, but not limited to, materials, shapes, sizes and/or diameters. Clearly, the number of permutations of device configurations is significant. Providing devices with such a composite construction allows for the manipulation of the device's properties to suite the intended application.

In an additional variation, the surface of the capturing portion can include a wire frame structure, a mesh, a single wound wire, a film, a membrane, a polymer covering, and a plurality of crossing wires or a heterogeneous mixing of these. In additional variations, a section of the capturing portion can include wires, while another section of the capturing portion can include a film. Clearly, any number of permutations is within the scope of this disclosure. In any case, the capturing surface should prevent the obstruction from escaping as the device is removed from the body. Clearly, the capturing surface can comprise any number of shapes or configurations.

As noted herein, the joint-less construction improves the flexibility and strength of the device by eliminating joints, connection points, or other attachment points. In addition, the joint-less construction improves the ability of the device to be delivered through a small microcatheter. As a result, the device and microcatheter are able to access remote regions of the vasculature.

The devices may be fabricated to be self-expanding upon deployment from a catheter. Alternatively, the devices can be constructed from shape-memory alloys such that they automatically deploy upon reaching a pre-determined transition temperature.

The devices of the present invention may also include features to prevent migration of the obstruction as the capturing portion encapsulates the obstruction. For example, a proximal foot (such as region of increased surface area) can be located on or in the catheter. In another variation, an additional capture portion is located on the catheter where the proximal end of this capture is a mesh, a single wound wire, a film, a membrane, a polymer covering, or a plurality of crossing wires affixed to or in the catheter. Accordingly, the capturing portions both envelope or surround the obstruction as they are moved together. As noted below, additional variations may allow for temporarily locking of the two capturing portions together for increase effectiveness in removing the obstruction from the body.

The operation of the devices and method described herein secure the obstruction, overcome the friction forces acting on the obstruction, and then remove the obstruction from the anatomy without losing or fractionating the obstruction. In one variation of the invention, this is accomplished by the obstruction removal device interacting with the obstruction in the following manner: (1) a catheter passes distal to the obstruction by passing either through the obstruction and/or between the obstruction and the vascular wall; (2) a first capturing portion is deployed distally to the obstruction and the catheter is withdrawn proximal to the obstruction; (3) the capturing portion is then translated over the obstruction by withdrawing the main bundle. Since the main bundle is affixed to a distal end of the capturing portion, misalignment between the bundle and the capturing portion does not cause distortion of the open proximal end. Since the open proximal end remains expanded against the lumen wall, the capturing portion can then be advanced over the obstruction.

The method and systems may also include the use of an additional capturing portion having an open distal end. This configuration allows the first capturing portion and second capturing portion to envelop or ensnare the obstruction from both the proximal and distal sides. Additional variations even allow for temporarily locking the two capturing portions together. Such a feature increases the ability to remove the obstruction from the body It should be noted that reference to surrounding, capturing or securing the obstruction includes partially and/or fully surrounding, engulfing, encapsulating, and/or securing the obstruction. In any case, a portion of the device engages the obstruction prior to translation of the obstruction within the lumen.

It should be noted that in some variations of the invention, all or some of the device can be designed to increase their ability to adhere to the obstruction. For example, the wires may be coupled to an energy source (e.g., RF, ultrasonic, or thermal energy) to "weld" to the obstruction. Application of energy to the device can allow the surrounding portion to deform into the obstruction and "embed" within the obstruction. Alternatively, the device can impart a positive charge to the obstruction to partially liquefy the obstruction sufficiently to allow for easier removal. In another variation, a negative charge could be applied to further build thrombus and nest the device for better pulling force. The wires can be made stickier by use of a hydrophilic substance(s), or by chemicals that would generate a chemical bond to the surface of the obstruction. Alternatively, the filaments may reduce the temperature of the obstruction to congeal or adhere to the obstruction.

Additional devices and methods for treating ischemic stroke are discussed in commonly assigned U.S. patent application Ser. No. 11/671,450 filed Feb. 5, 2007; Ser. No. 11/684,521 filed Mar. 9, 2007; Ser. No. 11/684,535 filed Mar. 9, 2007; Ser. No. 11/684,541 filed Mar. 9, 2007; Ser. No. 11/684,546 filed Mar. 9, 2007; Ser. No. 11/684,982 filed Mar. 12, 2007, Ser. No. 11/736,526 filed Apr. 17, 2007 and Ser. No. 11/736,537 filed Apr. 17, 2007; the entirety of each of which is incorporated by reference. The principles of the invention as discussed herein may be applied to the above referenced cases to produce devices useful in treating ischemic stroke. In other words, the wire-shaped construction of devices according to present invention may assume the shapes disclosed in the above-referenced cases when such a combination is not inconsistent with the features described herein.

BRIEF DESCRIPTION OF THE DRAWINGS

Each of the following figures diagrammatically illustrates aspects of the invention. Variation of the invention from the aspects shown in the figures is contemplated.

FIG. 3A illustrates a main bundle having a curved or shaped portion.

FIGS. 4C to 4E illustrate an overview of a variation of a delivery system employing a proximal and distal capturing portion.

FIG. 4F illustrates compression or collapsing of a proximal capturing portion about an obstruction prior to translation of the obstruction in the vessel.

FIGS. 6A to 6E illustrate an example of the removal of an obstruction from a body lumen using one variation of a system under the present invention.

FIGS. 7A to 7B illustrate coverings for use with capturing portions of the present invention.

FIGS. 8A to 8B illustrate an additional set of fibers within capturing portions, where the fibers improve retention of the clot within the device.

DETAILED DESCRIPTION

It is understood that the examples below discuss uses in the cerebral vasculature (namely the arteries). However, unless specifically noted, variations of the device and method are not limited to use in the cerebral vasculature. Instead, the invention may have applicability in various parts of the body. Moreover, the invention may be used in various procedures where the benefits of the method and/or device are desired.

Figure 1A:
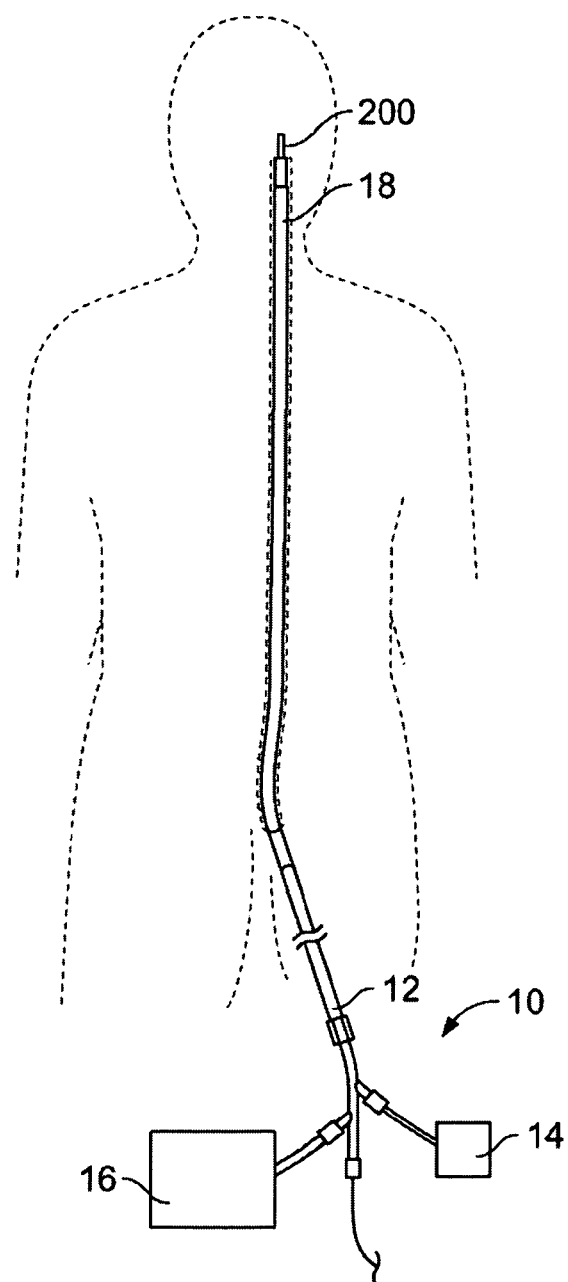
FIG. 1A illustrates an example of a device according to the present invention when used in a system for removing obstructions from body lumens.

FIG. 1A illustrates a system 10 for removing obstructions from body lumens as described herein. In the illustrated example, this variation of the system 10 is suited for removal of an obstruction in the cerebral vasculature. Typically, the system 10 includes a catheter 12 microcatheter, sheath, guide-catheter, or simple tube/sheath configuration for delivery of the obstruction removal device to the target anatomy. The catheter should be sufficient to deliver the device as discussed below. The catheter 12 may optionally include an inflatable balloon 18 for temporarily blocking blood flow or for expanding the vessel to release the obstruction.

It is noted that any number of catheters or microcatheters maybe used to locate the catheter/microcatheter 12 carrying the obstruction removal device 200 at the desired target site. Such techniques are well understood standard interventional catheterization techniques. Furthermore, the catheter 12 may be coupled to auxiliary or support components 14, 16 (e.g., energy controllers, power supplies, actuators for movement of the device(s), vacuum sources, inflation sources, sources for therapeutic substances, pressure monitoring, flow monitoring, various bio-chemical sensors, bio-chemical substance, etc.) Again, such components are within the scope of the system 10 described herein.

In addition, devices of the present invention may be packaged in kits including the components discussed above along with guiding catheters, various devices that assist in the stabilization or removal of the obstruction (e.g., proximal-assist devices that holds the proximal end of the obstruction in place preventing it from straying during removal or assisting in the removal of the obstruction), balloon-tipped guide catheters, dilators, etc.

Figure 1B:
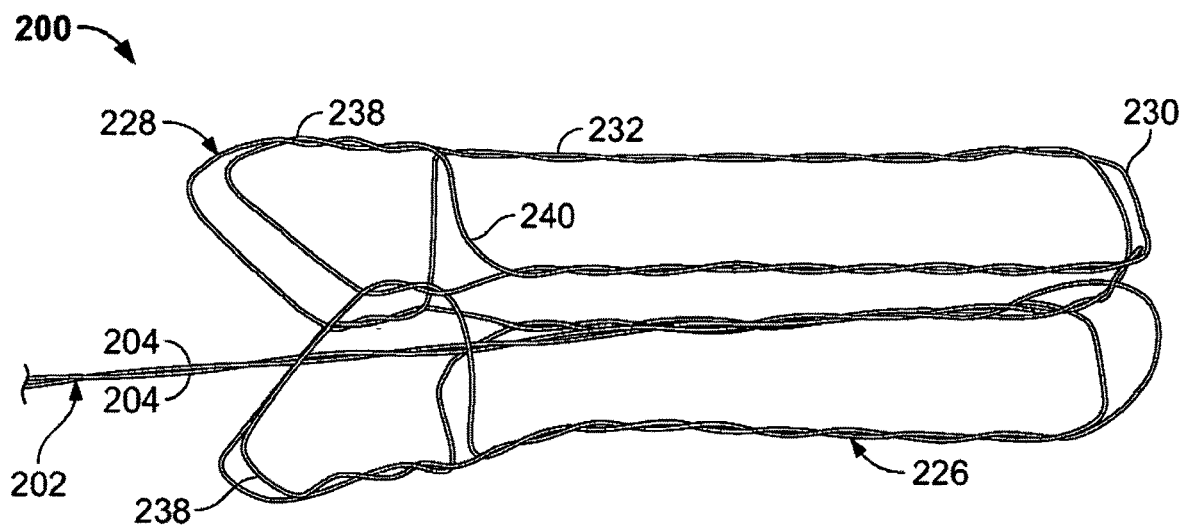
FIGS. 1B to 1D illustrates a first variation of the device having a joint-less construction of a capturing portion that articulates about a main bundle of wires.

FIG. 1B illustrates a first example of a device according to the features described herein. As shown, the device 200 generally includes a main bundle 202 comprising a group of individual wires 204. While the example shows the group consisting of two individual wires 204, the bundle may have any number of wires. In various examples 2, 4, or 8 wires were used to construct the device. In certain variations, the number of wires in the main bundle loop around from the capturing portion. For example, if 2 wires are used to construct the device, then when constructing the main bundle 2 wires are set to extend distally towards the capturing portion, where the 2 wires are then shaped to form the capturing portion. Eventually, the wires then loop back to extend proximally away from the capturing portion. Therefore, the 2 wires are doubled in the main bundle to create 4 separate wires in the main bundle.

The individual wires 204 themselves may be comprised of a number of different "micro" filaments, wires, or a single type of wire. Variations of the wires 204 are discussed in detail below; however, the wires 204 can be strands, filaments, or any similar structure that is able to be joined to form the device. The bundle 202 may be braided, wrapped, twisted, or joined in any manner such that they do not separate or become unbundled except where desired. For example, wires in any section of the device 200 can be bonded together (e.g., with epoxy, a polymeric coating, weld, solder, and/or adhesive, etc.) to prevent the wires from separating during deformation of the device as it deploys or removes the obstruction. In addition, the main bundle 202 can incorporate any number of features to assist in orienting the device 200 within the body passage. For example, the main bundle 202 can include a pre-set bend that would bias the capturing portion in a desired orientation upon deployment as discussed below (FIG. 2G).

The device 200 also includes a capturing portion 226. This capturing portion 226 may comprise such constructional designs as a basket, a filter, a bag, a coil, a helical wire structure, a mesh, a single wound wire, a film, a membrane, a polymer covering, or a plurality of crossing wires. In variations of the device, the capturing portion 226 is sufficiently permeable to allow blood or other fluid flow therethrough. As noted above, capturing portion 226 may be any structure that covers, encapsulates, engulfs, and/or ensnares the obstruction either fully or partially. Accordingly; although the capturing portion 226 is illustrated as a filter/bag, the wires may diverge to form a coil, helical shape, other mesh structure, or any other structure that defines a space that can be translated over the obstruction to ultimately remove the obstruction 2.

The capturing portion 226 includes an open proximal end 228, a permeable distal end 230 and a capturing surface 232 located therebetween. The surface 232 of the capturing portion 226 defines a volume, cavity, or space that is able to cover, encapsulate, envelop, engulf, ensnare and/or surround the obstruction. Generally, the term traversing wire or filament refers to the section of wire 204 that forms the capturing surface 232. Generally, the traversing wires form the capturing surface 232 and then form the open proximal end 228. As discussed herein and illustrated below, the open proximal end 228 expands within the lumen, typically to the lumen walls, so that the obstruction enters the open proximal end 228 as the bundle 202 translates the device 200 proximally. In most devices, the open proximal end 228 is designed to provide a low friction surface so that it translates over the obstruction without moving the obstruction significantly. The capturing surface 232 has an increased frictional surface so that it can capture and ultimately remove the obstruction. The frictional surface can also be described as a coverage density. In essence, as the frictional surface/coverage density increases, there is more "device" surface area to interact with the obstruction. In some variations the capturing surface has an increasing frictional surface between the open proximal end and the permeable distal end.

The permeable distal end 230 is typically sufficiently porous so that fluid or blood may flow through. However, the end 230 is sufficiently closed (or has an increased surface area) so that the obstruction should not escape through the distal end 230 of the device 200. The obstruction becomes ensnared within the capturing portion 226 and is prevented from passing through by the permeable distal end 230.

Figure 1C:
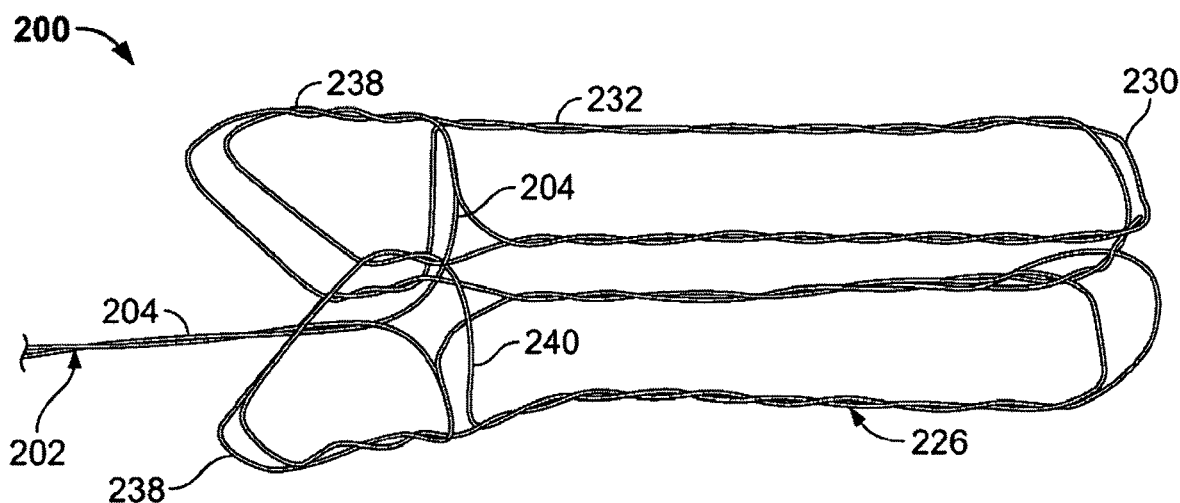

One important feature of the present devices is that the main bundle 202 and capturing portion 226 can articulate relative to one another without interfering with the size or profile of the open proximal end 228. This feature is described more fully in FIGS. 5A to 5B below. As shown, the main bundle 202 extends through the open proximal end 228 and through at least a portion of the capturing portion 226. In FIG. 1B, the main bundle 202 and the group of wires 204 branch or diverge at the permeable distal end 230 to form the capturing portion 226. In FIG. 1C, the main bundle 202 branch or diverge within a mid-portion or at the capturing surface 232 rather than at the permeable distal end 230. In such a case, the wires 204 form the capturing surface 232 first and ultimately branch to form the remainder of the capturing portion. In any case, by extending through the open proximal end 228, the main bundle 202 is able to articulate relative to the capturing portion 226 without significantly reducing a profile of the open distal end 228.

Figure 1D:
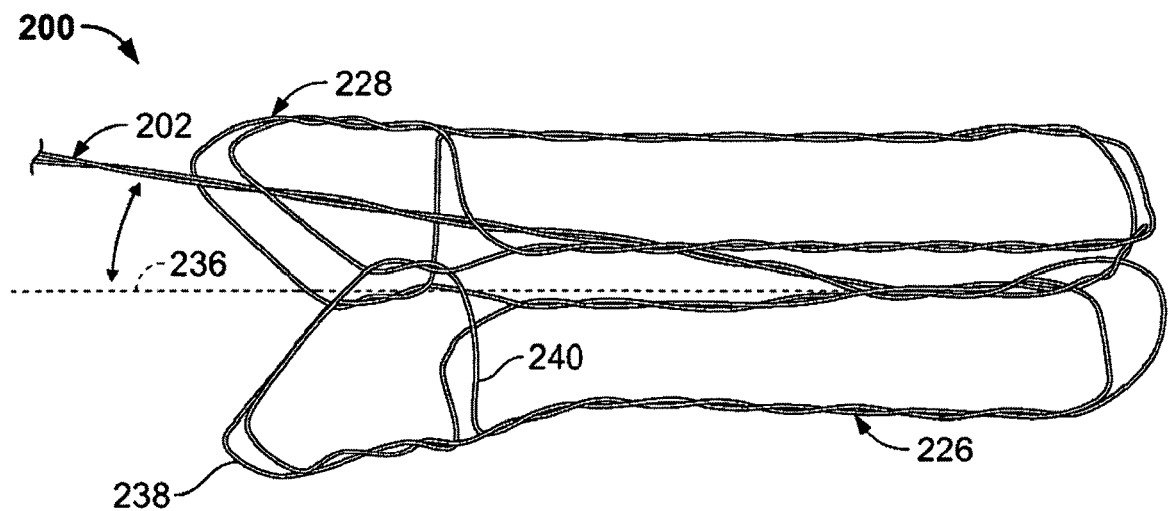

FIG. 1D illustrates a condition where the main bundle 202 and capturing portion 226 articulate relative to one-another. Because the main bundle 202 joins the capturing portion at a distance from the open proximal end movement of the main bundle 202 relative to an axis 236 of the capturing portion 226 does not reduce a profile of the open proximal end 228. If the main bundle 202 were affixed or connected to the open proximal end 228, then any movement of the bundle 202 away from the capturing portion's axis 236 would exert a force on the open end. This force, in turn, would cause the open end to narrow or deform. By doing so, the open end would not be able to uniformly expand against the lumen wall to capture the obstruction.

Turning now to the construction of the device 200, as shown in FIGS. 1B and 1C, the main bundle or a leading wire 202 extends beyond the open proximal end 228 and forms the capturing portion. In one variation, the construction of the device relies on converging/diverging wires to form continuous shapes so that the device is completely joint or connection free. However, as noted herein, the leading wire or main bundle 202 can be affixed to a structure that forms the capturing portion via an attachment point, joint, or junction. In addition, the structures forming the capturing portion can be fabricated from such processes as laser cutting of tubes, etching, metal injection molding, or any other such process.

The devices of the present invention can also include additional features to aid in removal of obstructions. For example, as shown in FIGS. 1B to 1C, the open proximal end 228 can include one or more petals or flanges 238 extending radially outward. The flanges 238 allow device 200 to have a flared structure at the open proximal end 228. In one example, the capturing portion 226 can be slightly oversized relative to the body passage containing the obstruction or slightly larger than the capturing portion. The flanges 238 provide an additional force against the wall of the passage to ensure that the device 200 is able to surround or encapsulate the obstruction. In yet another feature, in variations of a system having a proximal and distal capturing portion, the flanges can serve to lock the proximal and distal capturing portions together once they encapsulate or surround an obstruction. This feature minimizes the chance that the obstruction escapes from the capturing portions as the device and obstruction are removed from the body lumen.

In additional variations, the main bundle can diverge to form the capturing portion in multiple locations so long as the capturing portion's ability to articulate is not sacrificed. For example, the main bundle can diverge in several locations along the capturing surface (not shown).

FIGS. 1B to 1C also shows an integrally formed reinforcement ring 240 located along the length of the capturing surface 232 (i.e., on the traversing wires). The reinforcement ring 240 can be a separate or discrete ring located on or in the capturing surface 232. Alternatively, or in combination, the reinforcement ring 240 can be a ring shape that is integrally formed through arrangement of the wires 204 (as show in FIGS. 1B to 1C). The reinforcement ring 240 assists in expanding the device when deployed in the body lumen and/or prevents the device (e.g., the open proximal end) from collapsing as the device moves within the lumen to secure the obstruction. The reinforcement ring 240 can comprise a single wire, or a twisted pair of wires. Alternatively, the rings do not need to extend entirely circumferentially around the capturing surface. Instead, a reinforcement portion may extend between adjacent traversing wires but does not necessarily extend around the circumference of the capturing section. As noted herein, reinforcement portions may extend between adjacent traversing wires in multiple locations.

Figure 2A:
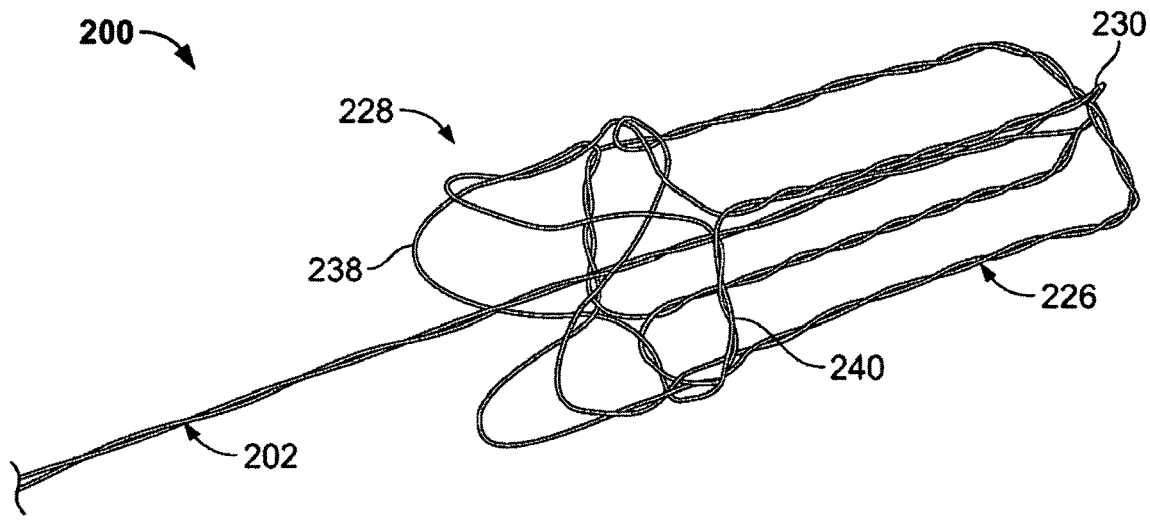
FIGS. 2A to 2L illustrate various constructions of capturing portions for use in the present invention.
Figure 2B:
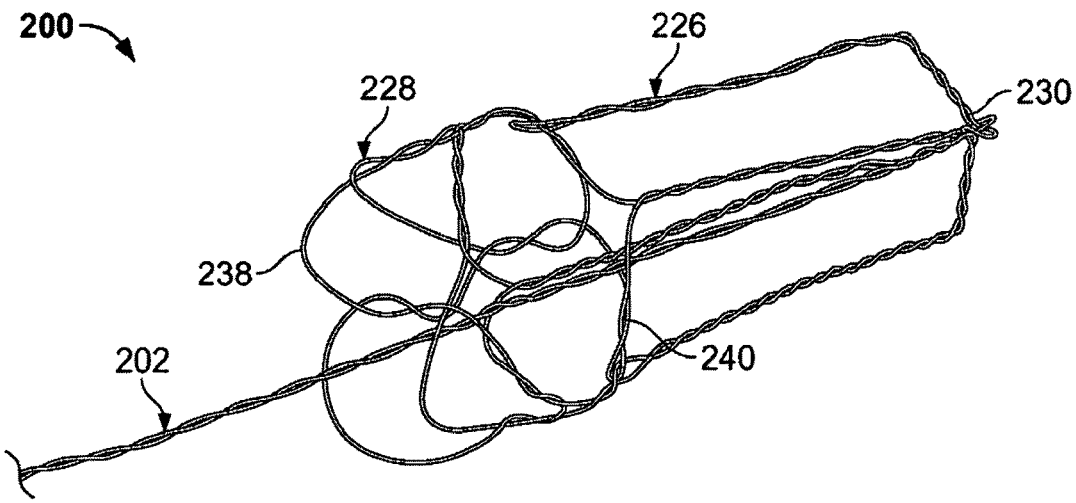
Figure 2C:
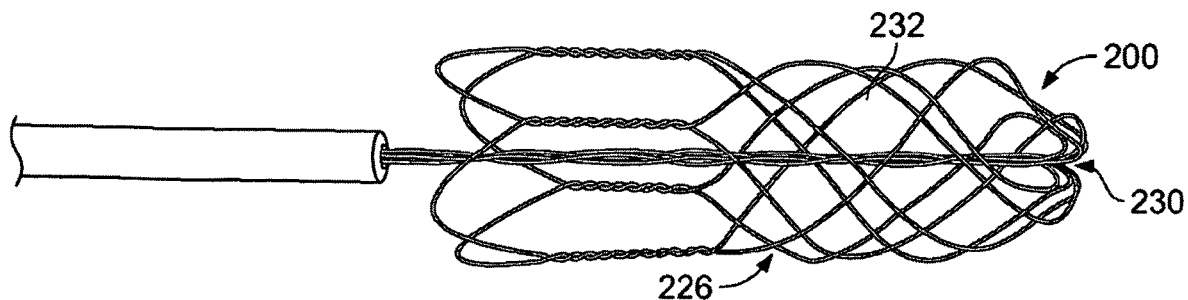
Figure 2D:
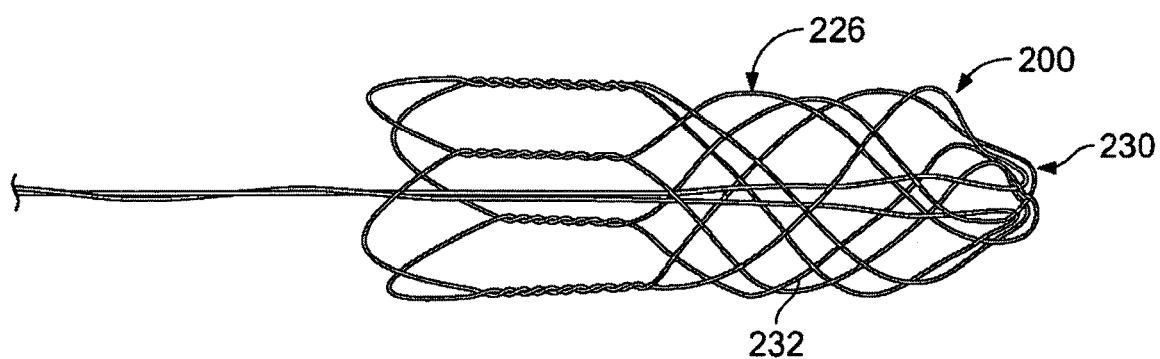
Figure 2E:
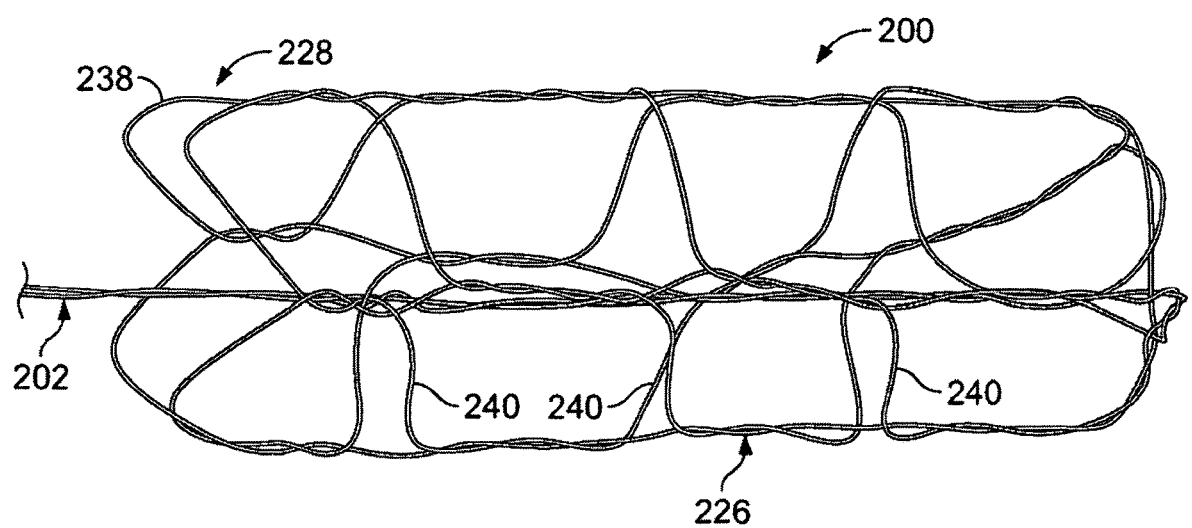
Figure 2F:
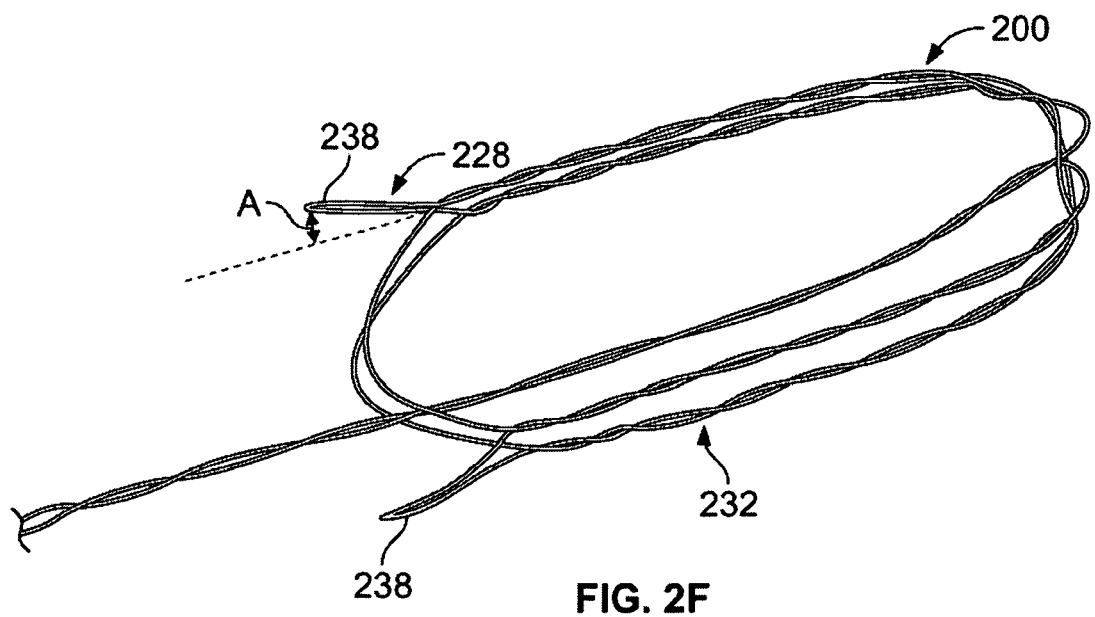
Figure 2G:
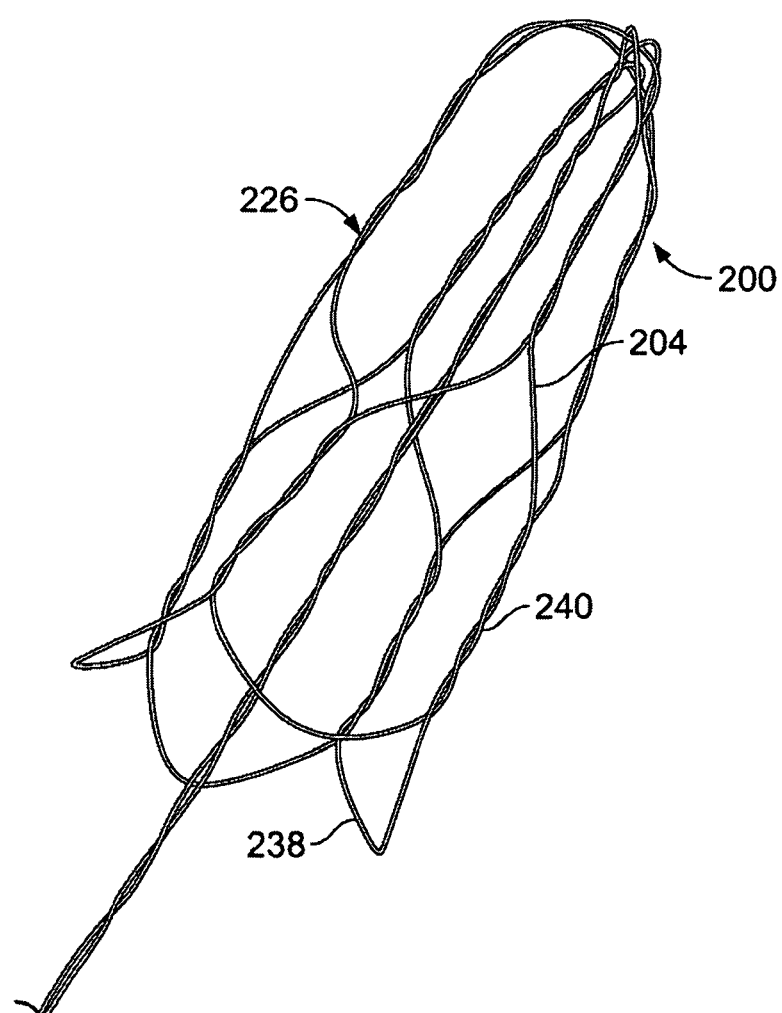

FIGS. 2A to 2L illustrate additional variations of capturing portions 226. FIG. 2A illustrates a variation having an integrated reinforcement ring 240. Typically, the reinforcement ring 240 provides radial strength to the capturing portion 226 to prevent collapse or deformation that would otherwise interfere with enveloping the obstruction. A reinforcement ring 240 may allow for use of wires that would otherwise provide unacceptable radial strength. For example, the reinforcement ring 240 may permit use of smaller diameter wires thereby allowing the device 200 to compress to a smaller diameter during delivery via a catheter.

In addition to the reinforcement ring 240, FIG. 2A includes an open proximal end 228 having a number of petals/flanges 228. In this variation, although the flanges 238 intersect one another, they are independently moveable.

FIG. 2B shows another variation of a device 200 where the capturing portion includes flanges 238 that are interwoven or connected with adjacent flanges 238. (Variations include bonding or otherwise joining the adjacent flanges together.) This feature provides the flanges 238 with a higher radial strength that reduces the likelihood that the flanges 238 bend or distort when moving in the body lumen or removing the obstruction.

FIG. 2C to 2D illustrate additional variations of devices having capturing portions 226 that have a basket type configuration. As shown, the capturing portions 226 and surface 232 comprise a denser mesh of traversing wires that ultimately lead to flanges 238 at the open proximal end 228. In such variations, a first portion of the capturing surface that is adjacent to the open proximal end has a low coverage density relative to the remaining portion of the capturing surface having a higher coverage density that eventually forms the permeable distal end 230. This construction lowers the lowering frictional resistance of the first portion of the capturing surface when moving over or against the obstruction but allows the remaining portion of the capturing surface to encapsulate and secure the obstruction.

As shown in FIG. 2C, the wires diverge from the main bundle towards the distal end of the capturing portion 226 to form the permeable distal end 230. The permeable distal end may actually have the same configuration as the capturing portion. In other words, the permeable distal end can simply be an extension of the capturing surface that extends over the distal end of the capturing portion.

Naturally, the divergence of the wires can occur over a length of the capturing portion 226 rather than immediately at the distal end. For example, as show in FIG. 2D, the wires diverge towards a mid-section of the capturing portion and ultimately form the permeable distal end 230.

FIG. 2E illustrates a variation of a device 200 having multiple reinforcement rings 240. As noted above, the reinforcement rings provide additional radial strength to the capturing portion 226 as the device 200 moves within the body lumen and prevents distortion of the capturing portion 226. The rings do not need to extend around an entire circumference of a device, variations include any number of supports that extend between adjacent traversing wires.

FIG. 2F illustrates an additional variation of a device 200 where the proximal flanges 238 taper or flare away from the capturing surface 232 by an angle A. The tapering of the flanges 238 improves the ability of the flanges 238 to contact a wall of the vessel or passage as the device 200 moves through the lumen. The angle A can be any angle. In addition, the angle A can be the same for all flanges 238. Alternatively, each flange 238 can have differing degrees of a taper with some flanges being relatively straight while others taper.

FIG. 2G shows a variation of a device 200 where traversing wires 204 forming the capturing surface 232 form a reinforcement structure 240 rather than a reinforcement ring as noted above. This configuration reduces the likelihood that the traversing wires 204 deform longitudinally, and less likely for the entire capturing portion 226 to collapse as it travels through tortuous anatomy.

Figure 2H:
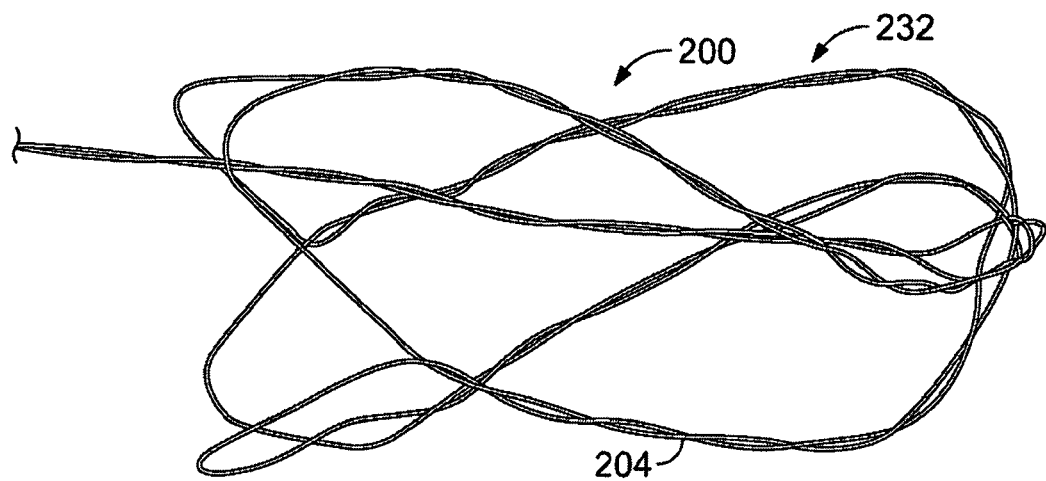

FIG. 2H shows a variation of a device 200 where the traversing wires 204 twist when forming the capturing surface 232. The device can be constructed starting with a non-twisting design, as shown above, and then twisted (i.e. where one end of the capturing portion 226 rotates relative to another end). The final twisted shape can be heat set to hold the shape. Alternatively, the capturing surface can simply be constructed into a twisted shape. This design provides advantages as the twisted nature of the capturing surface 232 should translate over the obstruction with less effort due to the torque-like motion of wires 204 as the physician pulls the device 200 over the obstruction. The twisting motion or torque helps reduce the static friction to a greater degree and generally increases the momentum of the capturing portion 226. Simply pulling this variation of the device in a proximal direction causes the twisted traversing wires 204 to translate longitudinally and rotationally over the obstruction in the same manner as if torque were being applied to the device 200.

The twisting configuration shown in FIG. 2H is also less likely to collapse as it goes around a bend in a vessel or other body lumen. Each traversing wire 204 travels in and out of a plane of the direction of travel of the device. This minimizes the contact between the traversing wire 204 and the wall of the body passage as the device 200 travels around a curve in the body passage.

Figure 2I:
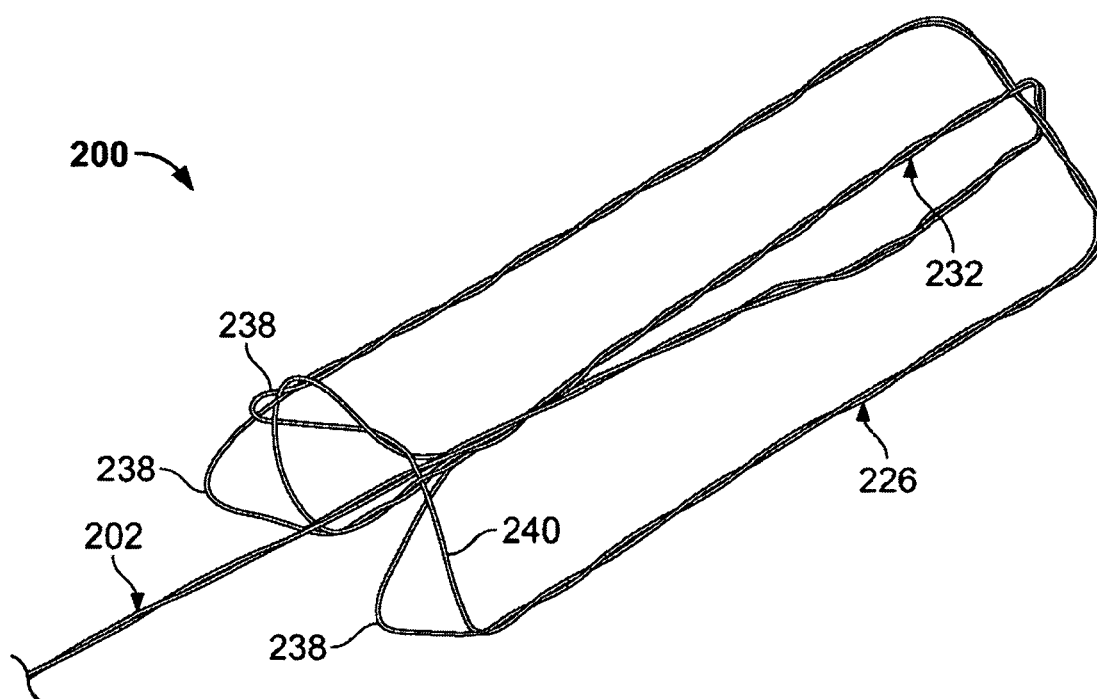

FIG. 2I shows a variation of a device 200 where capturing surface 232 of the capturing portion 226 has an "open side" (i.e., the capturing surface 232 does not circumferentially surround the main bundle 202. Accordingly, the reinforcement ring 240 and flanges 230 do not fully surround the main bundle 202 as well. As a result, in this variation the capturing portion 226 only includes 3 sides and 3 corresponding flanges 238. It is believed that this "open sided" design better conforms to the inner diameter of a vessel.

Figure 2J:
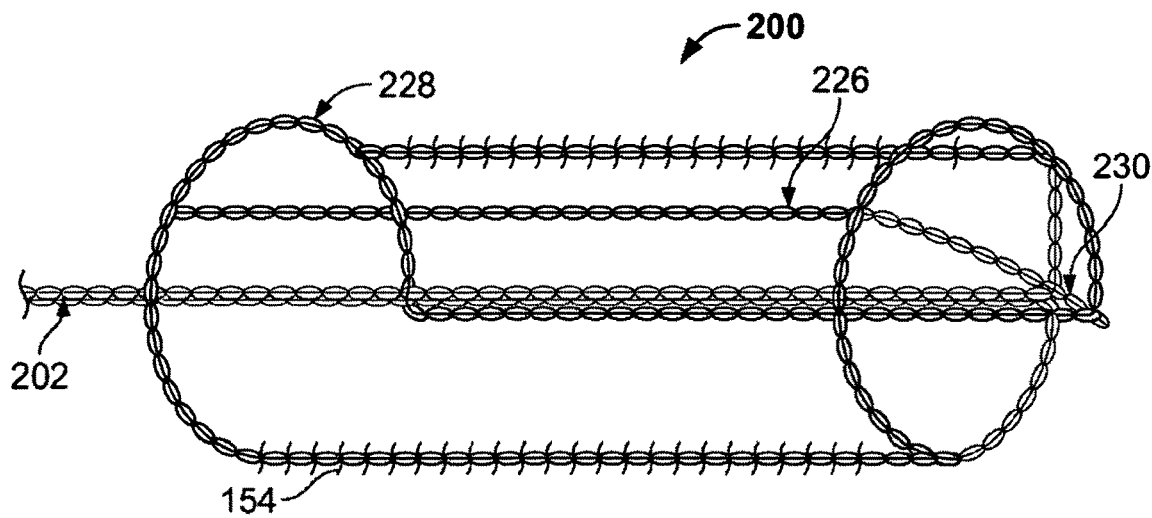

FIG. 2J illustrates another variation of a device 200 where the capturing surface portion 232 of the device 200 has an open side. The open side construction reduces friction between the device and the body lumen and between the device and the obstruction. In an additional variation, the openings in the proximal and distal end can be oriented in any configuration. For example, the openings can be 180 degrees rotated from one another. In addition, it is desirable to over-size the profile of the device relative to the diameter of the body lumen. An open ended, semi-circular or partial circular sectional profile makes it easier to oversize the device for the intended body passage and allows the device to better conform to the size of the vessel. In such cases, the capturing portion is open at one side of the device to allow the capturing portion to better expand against the vessel. As shown, the main bundle 202 extends through the capturing portion 226 to the permeable distal end 230. In this variation, the device 200 is not shown with petals/flanges on the open proximal end 228. However, petals can be incorporated into the design on all sides except for the open side.

As shown, the device includes mechanical features that assist in removal of the obstruction. These features can be hooks, fibers, barb, or any such structure. For example, such mechanical features are illustrated on FIG. 2J. Any portion of the capturing portion or even the device can have such hooks, fibers, or barbs 154 that grip into the obstruction as the device surrounds the obstruction. It will be important that such features prevent the obstruction from sliding proximally but do not hinder the ability of the practitioner to remove the device from the body.

Figure 2K:
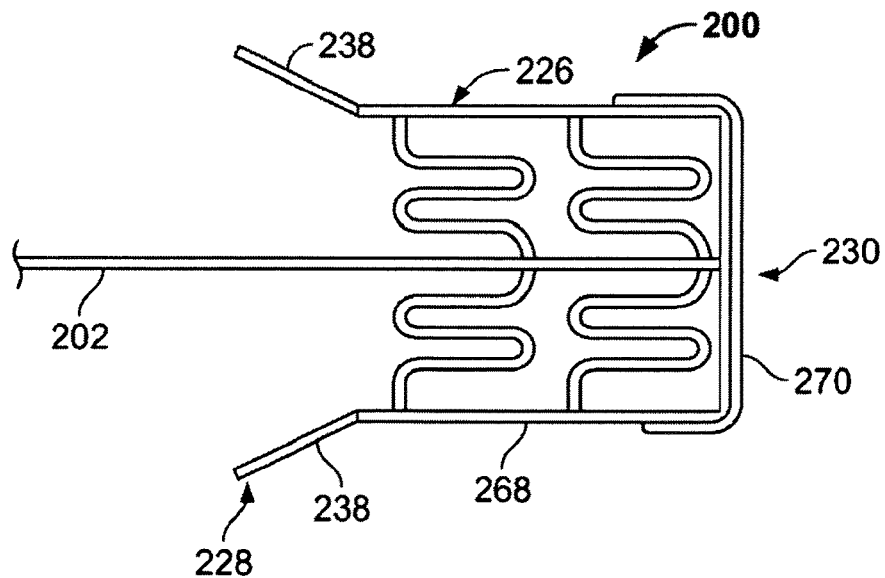

FIG. 2K illustrates another variation of a device 200 having a wire 202 extending to a distal end 230 of a capturing portion 226. In this variation the capturing portion 226 is fabricated from a stent-type structure. As noted above, it is within the scope of this disclosure to use any type of similar structure such as a laser cut tube, a chemically etched or photo etched tube, a polymer or metal injection molded structure, a basket, a filter, a bag, a coil, a helical wire structures a mesh, a single wound wire, a film, a membrane, a polymer covering, or a plurality of crossing wires as the capturing portion 226 so long as the device can be compressed to a small size for delivery and expand after traversing the obstruction. The illustrated variation also shows a covering 270 located on the distal end 230 of the capturing portion 226. The length of the polymeric covering 270 can vary across the capturing portion 226 to prevent the obstruction from escaping as the device is translated over the obstruction. Furthermore, the covering 270 can be polymeric or a wire mesh. However, typically the covering has sufficient porosity to allow blood to flow through the device 200.

Figure 2L:
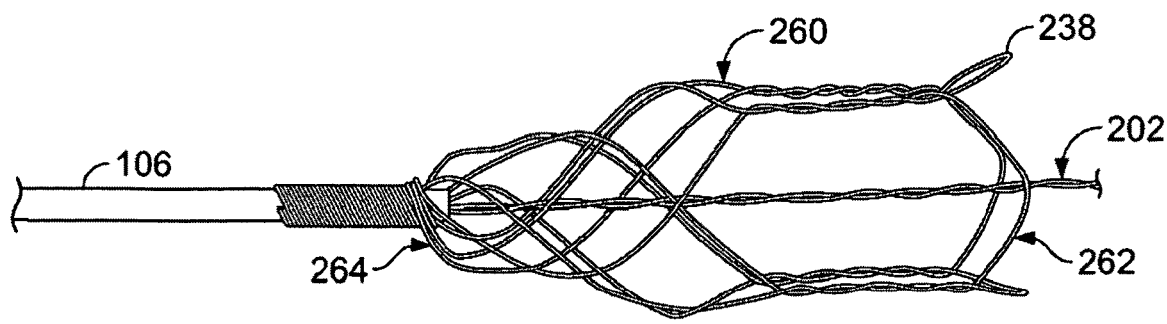

FIG. 2L illustrates another feature for use with system described herein. In this variation, the system includes a proximal capturing portion 260 located on an exterior of a delivery sheath 106. The main bundle 202 extends through the sheath 106 to a distal capturing portion (not shown). As discussed below, the proximal capturing portion 260 can be similar to the distal capturing portions 226 described herein with the exception that the distal end 262 of the proximal capturing portion is open while the proximal end 264 of the proximal capturing portion is closed. Furthermore, the proximal capturing portion 260 articulates with respect to the sheath 106 much in the same manner as the distal capturing portion 226 articulates relative to the main bundle 202. In this variation, the proximal end 264 of the proximal capturing portion 260 is tapered or has a smaller profile than the remaining proximal capturing portion 260. Such a feature may be useful to improve the deliverability of the device to the intended site as well as to maneuver around any obstructions within the body passage. In addition, as noted below (see e.g., FIG. 4F), the proximal capturing portion 260 can be compressed about the obstruction to improve the ability of the system to remove the obstruction.

FIG. 3A illustrates the main bundle 202 as having a curved or bend portion 252. This pre-set shape assists in orienting the capturing portion 226 within the body passage since the bend will cause the device to bias against a wall of the body passage.

Figure 3B:
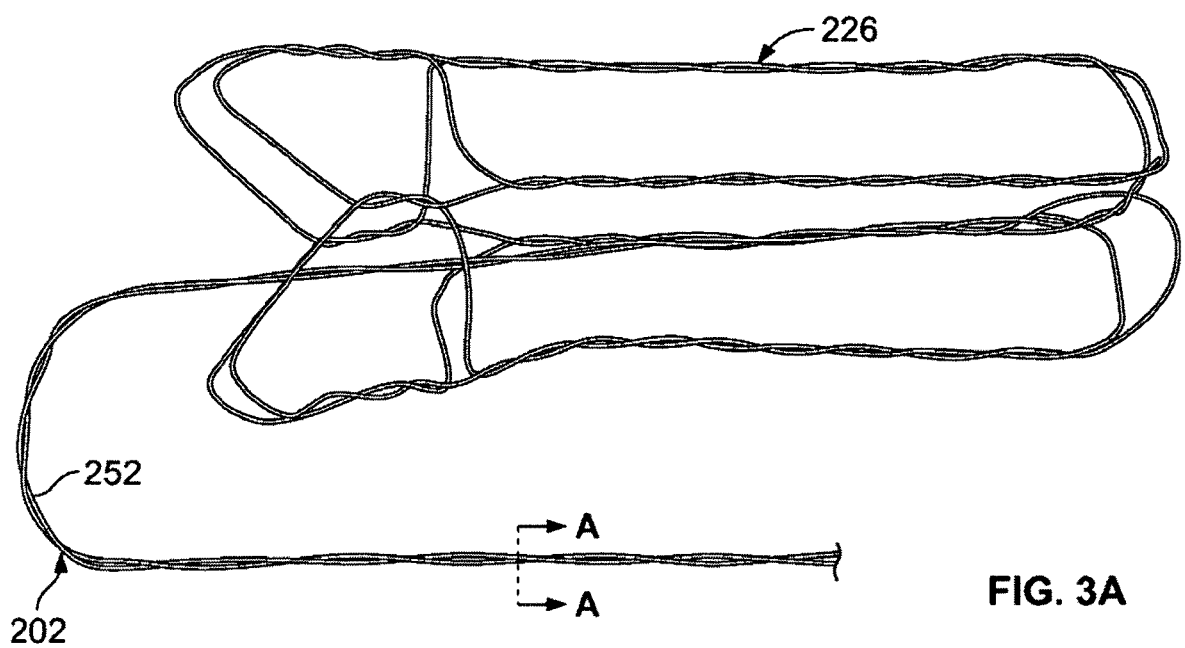
FIGS. 3B to 3D illustrate wires of different constructions within a main bundle.
Figure 3B:
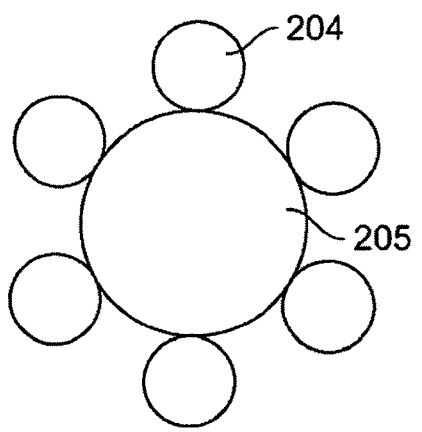
Figure 3C:
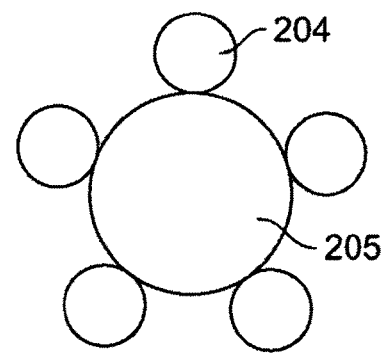

FIGS. 3B and 3C show cross sectional views taken along the line A-A in FIG. 3A. As shown, the wire form construction described herein allows for a number of configurations depending on the particular application. For example, the individual wires 204 (as shown in FIG. 1B) may themselves comprise a bundle of smaller wires or filaments. In addition, the wires can be selected from materials such as stainless steel, titanium, platinum, gold, iridium, tantalum, nitinol, alloys, and/or polymeric strands. In addition, the wires used in a device may comprise a heterogeneous structure by using combinations of wires of different materials to produce a device having the particular desired properties. For example, one or more wires in the device may comprise a shape memory or superelastic alloy to impart predetermined shapes or resiliency to the device. In some variations, the mechanical properties of select wires can be altered. In such a case, the select wires can be treated to alter properties including: brittleness, ductility, elasticity, hardness, malleability, plasticity, strength, and toughness.

The device may include a number of radiopaque wires, such as gold and platinum for improved visibility under fluoroscopic imaging. In other words, any combination of materials may be incorporated into the device. In addition to the materials, the size of the wires may vary as needed. For example, the diameters of the wires may be the same or may vary as needed.

In addition, the individual wires may have cross-sectional shapes ranging from circular, oval, d-shaped, rectangular shape, etc. FIG. 3B illustrates one possible variation in which a number of circular wires 204 are included with a d-shaped wire 205. Moreover, the device is not limited to having wires having the same cross-sectional shape or size. Instead, the device can have wires having different cross-sectional shapes. For example, as shown in FIG. 3C, one or more wires 205 can have a different cross-sectional shape or size than a reminder of the wires 204. Clearly, any number of variations is within the scope of this disclosure.

To illustrate one such example, a device can have 8-12 wires made of 0.003" round superelastic material (e.g., nitinol). The device may additionally have 2-4 wires made from 0.002" platinum for fluoroscopy. Of the 8-12 nitinol wires, 1-4 of these wires can be made of a larger diameter or different cross-section to increase the overall strength of the device. Finally, a couple of polymer fibers can be added where the fibers have a desired surface property for clot adherence, etc. Such a combination of wires provides a composite device with properties not conventionally possible in view of other formation means (such as laser cutting or etching the shape from a tube or joining materials with welds, etc.). Clearly, any number of permutations is possible given the principles of the invention.

In another example, the device may be fabricated from wires formed from a polymeric material or composite blend of polymeric materials. The polymeric composite can be selected such that it is very floppy until it is exposed to either the body fluids and or some other delivered activator that causes the polymer to further polymerize or stiffen for strength. Various coatings could protect the polymer from further polymerizing before the device is properly placed. The coatings could provide a specific duration for placement (e.g., 5 minutes) after which the covering degrades or is activated with an agent (that doesn't affect the surrounding tissues) allowing the device to increase in stiffness so that it doesn't stretch as the thrombus is pulled out. For example, shape memory polymers would allow the device to increase in stiffness.

Figure 3D:
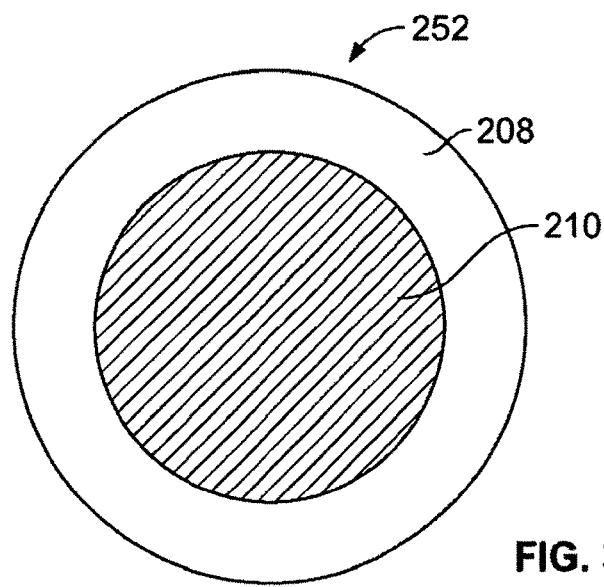

In another variation, one or more of the wires used in the device may comprise a Drawn Filled Tube (DFT) such as those provided by Fort Wayne Metals, Fort Wayne, Ind. As shown in FIG. 3D, such a DFT wire 252 comprise a first material or shell 208 over a second material 210 having properties different from the outer shell. While a variety of materials can be used, one variation under the present devices includes a DFT wire having a superelastic (e.g., Nitinol) outer tube with a radiopaque material within the super-elastic outer shell. For example, the radiopaque material can include any commercially used radiopaque material, including but not limited to platinum, iridium, gold, tantalum, or similar alloy. One benefit of making a capturing portion from the DFT wire noted above, is that rather than having one or more markers over the capturing portion, the entire capturing portion can be fabricated from a super-elastic material while, at the same time, the super-elastic capturing portion is made radiopaque given the core of radiopaque material within the super-elastic shell. Clearly, any composite DFT wire 252 can be incorporated into the system and capturing portions described herein.

Figure 4A:
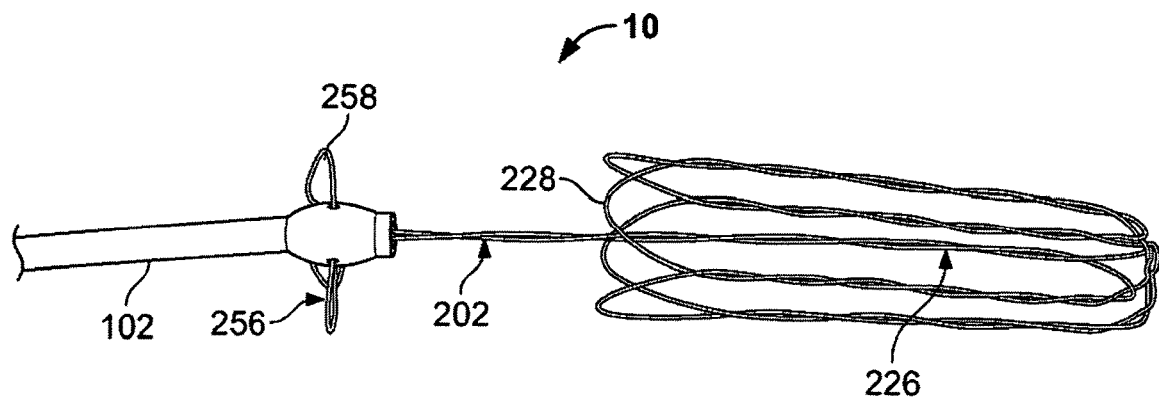
FIG. 4A illustrates am example of a proximal foot located on a catheter of the present system.

FIG. 4A shows a working end of a system 10 for removing an obstruction from a body lumen. In this variation, the system 10 includes a main bundle 202 and capturing portion 226 extending out of a micro-catheter or catheter 102. The micro-catheter 102 can optionally include a proximal foot 256 that can slide axially over main bundle 202 and can be variably positioned in relation to the capturing portion 226. The proximal foot 256 can include any number of configurations apart from the petal/flange 258 configuration (i.e., the foot can be a balloon, coil, shoulder, etc. where such structures simply replace the petals in FIG. 4A). In any case, the proximal foot 256 provides an increased surface area that provides an opposing force to the capturing portion 226, where the opposing force aids the movement of the obstruction within the capturing portion 226. Alternatively, the proximal foot stabilizes the obstruction and keeps the obstruction from moving with the capturing portion until the capturing portion envelops the obstruction.

The size of the proximal foot 256 can be adjusted depending on the target site anatomy. For example, a larger surface area can be employed if the target site is within a bifurcation of the body passage. The size of the proximal foot 256 can also be adjustable during the procedure. For example, in the case of a petal/flange 258 configuration, the petals 258 can assume a larger size to initially stabilize the obstruction and then reduce in size to allow the obstruction to be completely engulfed by capturing section 226.

The proximal foot 256 can extend from an interior of the catheter 102, such as from within the internal lumen of the catheter, or from an additional lumen within a wall of the catheter. Alternatively, the proximal foot 256 can be permanently affixed to the catheter 102. In such a case, a separate catheter (without a proximal foot) can be employed to traverse the obstruction for deployment of the device distally to the obstruction. Once the device is deployed, the catheters can be exchanged to provide the proximal foot. In an additional variation, the proximal foot 256 can be affixed to a delivery sheath (as described below) and be collapsed within the catheter, where advancement out of the catheter expands the proximal foot 256 so that it may function as described above.

Figure 4B:
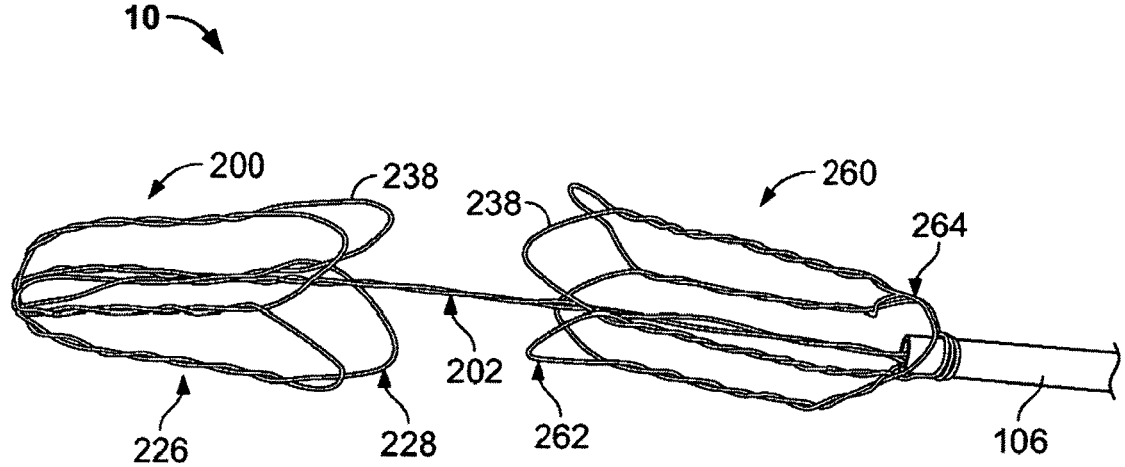
FIG. 4B illustrates a distal and a proximal capturing portion located on a system under the present invention.

FIG. 4B illustrates another variation of the system 10 where the system includes a proximal capturing portion 260 located on an exterior of a delivery sheath 106. Naturally, the proximal capturing portion 260 could also be affixed to an exterior of a micro-catheter. The proximal capturing portion 260 is similar to the capturing portions 226 described herein with the exception that the distal end 262 of the proximal capturing portion is open while the proximal end 264 of the proximal capturing portion is closed. In this variation, the capturing portion 226 and main bundle 202 move relative to the proximal capturing portion 260 to capture an obstruction. Furthermore, the proximal capturing portion 260 articulates with respect to the sheath 106 much in the same manner as the distal capturing portion 226 articulates relative to the main bundle 202. As shown, the petals 238 on the open ends 228 and 262 can interact to nest once the capturing portions 226 and 260 are moved sufficiently close to one another. The outward force caused by the retained obstruction provides a frictional interaction between adjacent petals/flanges 238 to maintain the nesting. Variations of the device include additional structures, such as springs, hooks, barbs, etc, to cause the open ends 228 and 262 to interlock. As noted above, a separate catheter can be used to initially deploy the capturing portion 226 beyond the obstruction. Although the capturing portions shown have the same configuration, the capturing portions 226 and 260 used in any given system do not have to match in size, shape, and configuration. For example, the proximal capturing portion can be impermeable to flow while the distal capturing portion allows flow. In another example, one basket may be undersized relative to the other to improve nesting.

In any case, the construction of the system 10 shown in FIG. 4B includes open ends 228 and 262 of capturing portions 226 and 260 that are unconnected. Accordingly, as the capturing portions 226 and 260 move towards one another as a result of the main bundle 202 translating relative to the delivery sheath 106 the open ends are free to articulate around the main bundle 202 and delivery sheath 106 respectively to remain expanded against the lumen wall.

Figure 4C:
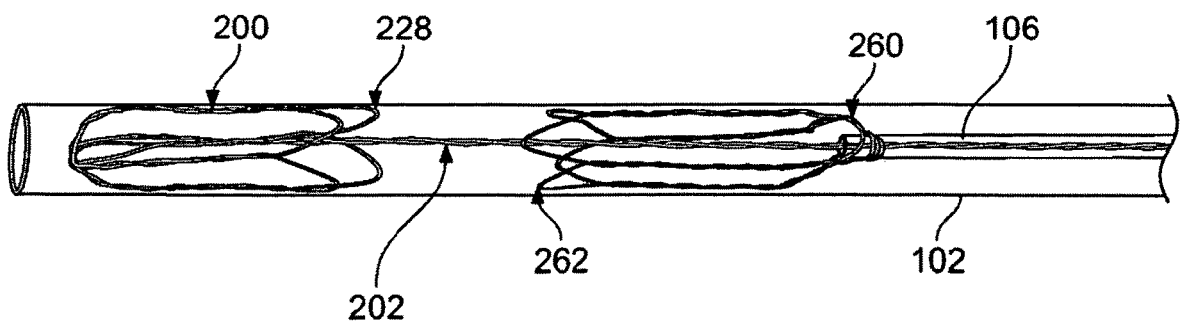

FIGS. 4C to 4E illustrate a variation of a system for delivery of the capturing portions 220 and 260. FIG. 4C shows the proximal 260 capturing portion affixed to a delivery sheath 106. In alternate variations, the proximal capturing portion 260 can be replaced with a proximal foot (not shown). As noted above, the main bundle or leading wire 202 extends through the delivery sheath 106 and connects to the distal capturing portion 200 beyond the opening 228 of the distal capturing portion 200. The main bundle or leading wire 202 extends through the proximal capturing portion 260. This allows the free ends of the capturing portions 228 and 262 to remain relatively unattached so that they can articulate and conform to the curvature of the vessels (see below, especially FIGS. 5A to 6E). The capturing portions 200 and 260, main bundle 202 and delivery sheath 106 extend through a microcatheter 102.

FIG. 4D illustrates a state of deployment after the microcatheter 102 traverses the obstruction (not shown). Once the microcatheter 102 is distal to the obstruction, the distal capturing portion 200 deploys from the end of the microcatheter 202. As noted herein, the capturing portions can self-expand or can expand upon actuation by the physician. In any case, the distal capturing portion 200 should be sufficiently collapsible to remain within the microcatheter 102 for deployment distal to an obstruction. To deploy the distal capturing portion 200 from the catheter 102, the main bundle 202 can translate to push the distal capturing portion 200 to eject it from the catheter 102. Alternatively, the microcatheter 102 can be withdrawn from the distal capturing portion 200.

FIG. 4E illustrates the deployment state after the catheter 102 is withdrawn proximal to the obstruction and after the proximal capture portion 260 is delivered from the microcatheter 102. As noted above, the proximal capture portion 260 can be affixed to an exterior of the catheter, in which case the catheter may be either de-sheathed or exchanged. Alternatively, and as shown, the proximal capturing portion 260 is affixed to a delivery sheath 106 and is fabricated to collapse within the microcatheter for ultimate deployment, whereby translating the sheath 106 delivers the proximal portion 260 from the microcatheter.

FIG. 4F shows another aspect of the system 10 where the proximal end 264 of the proximal capturing portion 260 is collapsed or compressed about an obstruction 2 prior to translation of the obstruction 2 within the vessel. In this illustration, the proximal capturing portion 260 is compressible by advancing the catheter 102 over the closed proximal end 264 of the capturing portion 260. In such a case, the proximal capturing portion 260 is slidable within and relative to the catheter 102. Naturally, variations may include compressing the proximal end 264 during translation of the obstruction 2. In either case, the proximal capturing portion 260 can be compressed in a number of different ways. For instance, the proximal basket can be compressed using a catheter 102 (as shown), or the delivery sheath 106, or any other number of mechanisms (not illustrated).

As shown, the proximal end 264 can be compressed using a sheath 106. However, other means of compressing may be employed (e.g., a loop structure, a tube over the sheath, a draw-string configuration, etc.) In use, once the distal capturing portion 200 is deployed distally to the obstruction 2 and the catheter 102 is withdrawn proximal to the obstruction 2, the proximal capturing portion 260 is deployed. As the proximal capturing portion 260 partially (or totally) engulfs the obstruction 2, the physician can collapse or compress the proximal capturing portion 260 to better secure the obstruction within the system 10.

It is noted that any number of shapes, configurations, as well as any number of joined wires may be contemplated to form devices under the present disclosure. However, variations of the invention include selecting a number of wires to produce specific structural properties to the device. For example, the devices can have any number of wires where the limit is determined by the ability to produce a device of a sufficiently small size to access the area containing the obstruction. However, in some cases, it may be desired that wires are chosen to impart specified characteristics. For example, in the illustrated variation, the main bundle may comprise any number of wires that do not diverge to form subsequent shapes in the device. In other words, not all of the wires forming a section are required to diverge to form an adjacent section. Instead, these non-diverging wires may simply "loop" back away from the device. In an additional variation, one or more wires may diverge to form a particular portion of the capturing portion (e.g., the closed end, traversing wires, etc.). Then the wires can loop back to converge again with the main bundle.

Figure 5A:
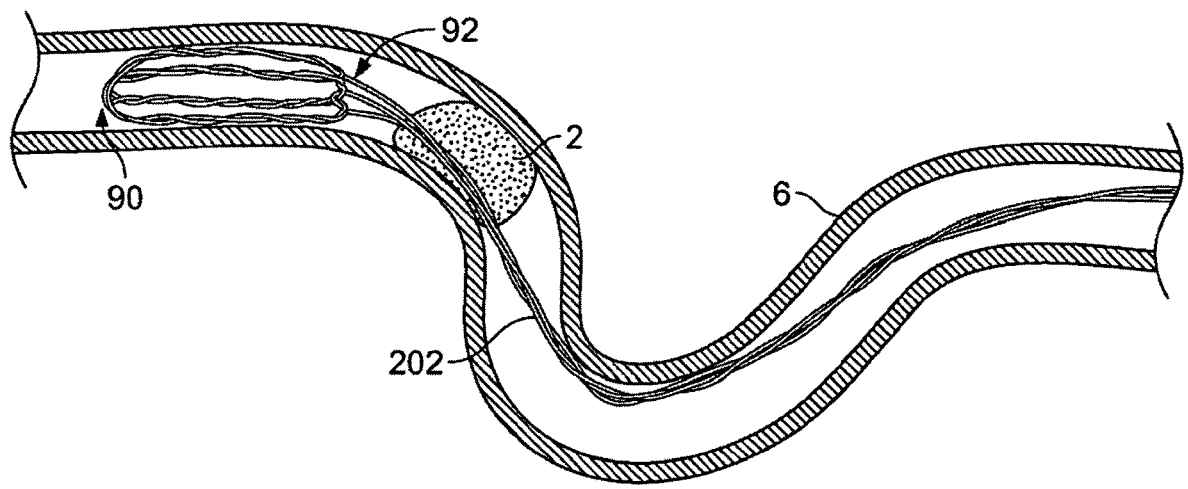
FIG. 5A illustrates closure of the proximal opening of a capturing portion without the benefit of articulation of the capturing portion about a leading wire.
Figure 5B:
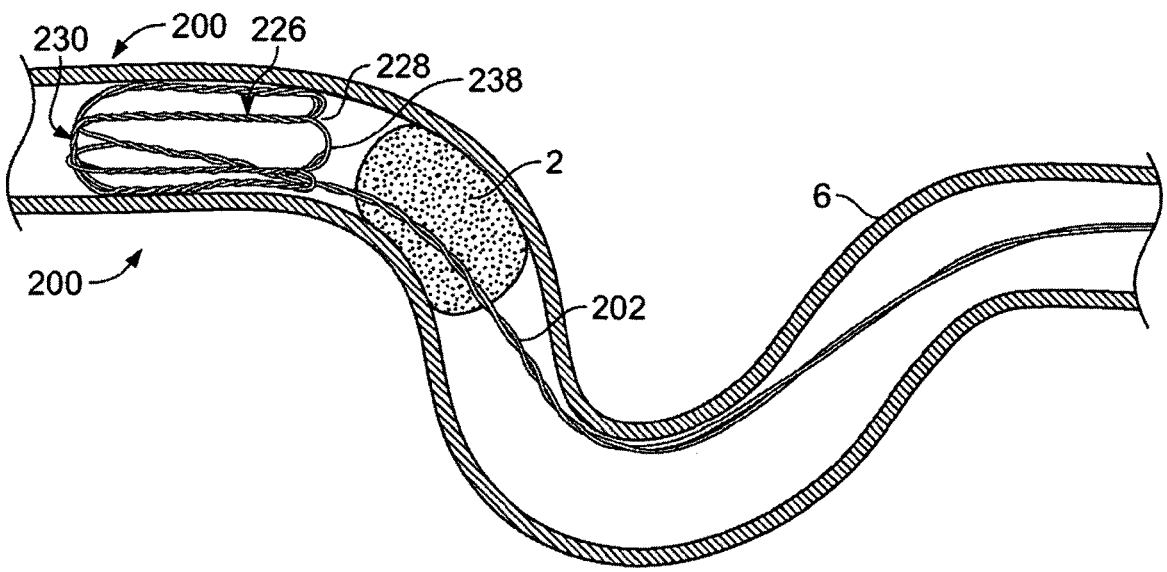
FIG. 5B illustrates, conceptually, one benefit of articulation of a capturing portion about a leading wire or main bundle of wires.

FIGS. 5A to 5B illustrate one benefit of affixing a leading wire or bundle of wires 202 beyond a proximal opening 228 of a capturing portion 226. FIG. 5A illustrates a basket type structure 90 where a wire 202 is affixed to a proximal end 92. As shown, as the leading wire 202 pulls the basket 90 through tortuous anatomy 6, the force component pulling away from an axis of the device 90 causes the proximal open end 92 to constrict or reduce in size. As shown, as the proximal end 92 approaches the obstruction 2 the perimeter of the end is not placed against the walls of the body passage 6. As a result, the constricted opening 92 places an increased axial force on the obstruction 2 as the basket 90 translates over the obstruction 2 (because the proximal end 92 pushes against the obstruction rather than sliding around it), making encapsulation of the obstruction more difficult and possible leading to vascular damage.

FIG. 5B shows a device 200 according to the principles disclosed herein. The leading wire 202 is affixed to the distal end 230 of the capturing portion 226. As the main bundle 202 is pulled through the curved vascular path, the capturing portion 226 pivots or articulates about the bundle 202 and remains aligned with the axis of the vessel. As a result any misalignment between the leading wire 202 and an axis of the capturing portion 226 does not affect the open proximal end 228. As noted above, some closing of the open proximal end may occur, though it will not be sufficient to interfere with the obstruction as the capturing portion moves over the obstruction. Such a configuration allows the perimeter of the open proximal end 228 to remain against the wall of the passage 6. As shown, because the open proximal end 228 is not constricted, the open proximal end 228 is better suited to slide around the obstruction for eventual removal.

FIGS. 6A to 6E show one example of the deployment of a variation of a device according to the present invention about an obstruction in a vessel. The figures are intended to demonstrate the initial placement of the device immediately prior to removal of the obstruction.

Figure 6A:
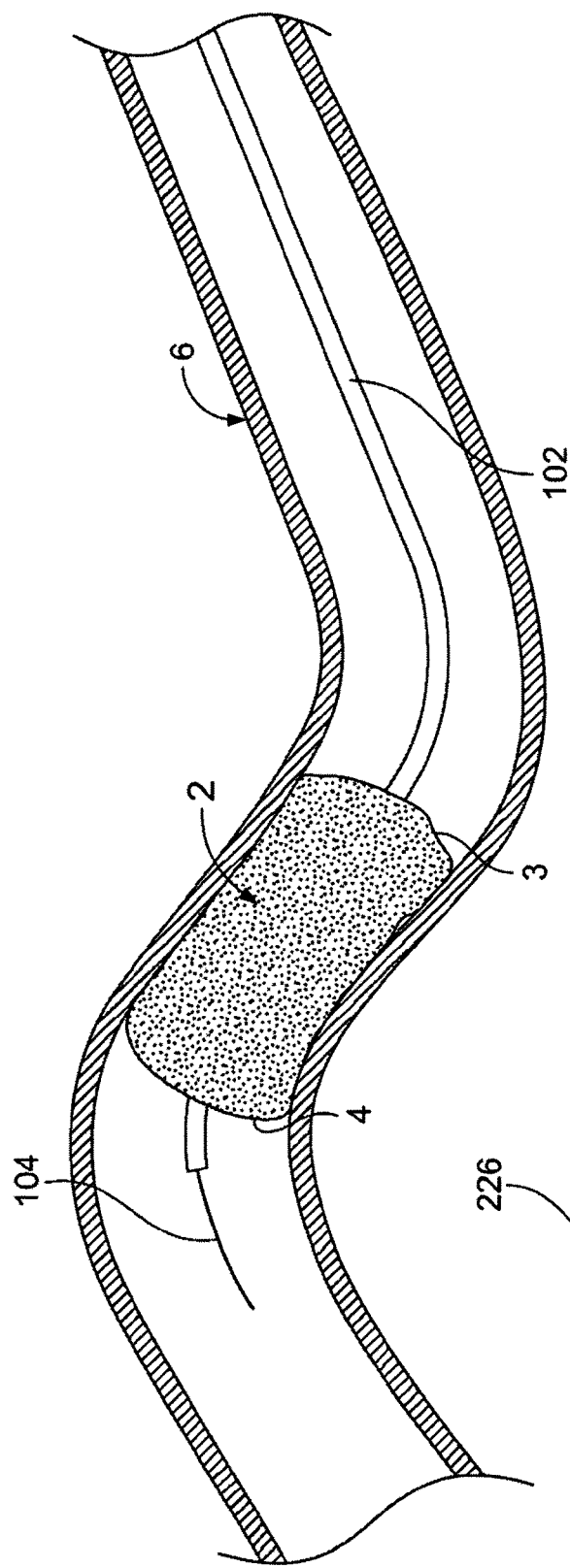

FIG. 6A illustrates an obstruction 2 lodged within a body lumen or vessel 6. In the case where the vessel is a cerebral artery, the obstruction may result in an ischemic stroke. Using standard interventional catheterization techniques, a microcatheter 102 and guidewire 104 traverse the obstruction. The microcatheter 102 may be advanced through the obstruction 2. Alternatively, the microcatheter 102 may "push" aside the obstruction and is advanced around the obstruction. In any case, the microcatheter 102 travels from the near end 3 (or proximal side) of the obstruction 2 to the far end 4 (or distal side) of the obstruction 2. It is noted that the catheter 102 may be centered or off-center with respect to the obstruction 2. Furthermore, the device may or may not be used with a guidewire to navigate to the site and traverse the obstruction.

Some variations of the device may be placed without an accompanying guidewire. Moreover, the structures discussed herein may be directly incorporated into a guidewire assembly where deployment may require a sheath or other covering to release the components from constraint.

Figure 6B:
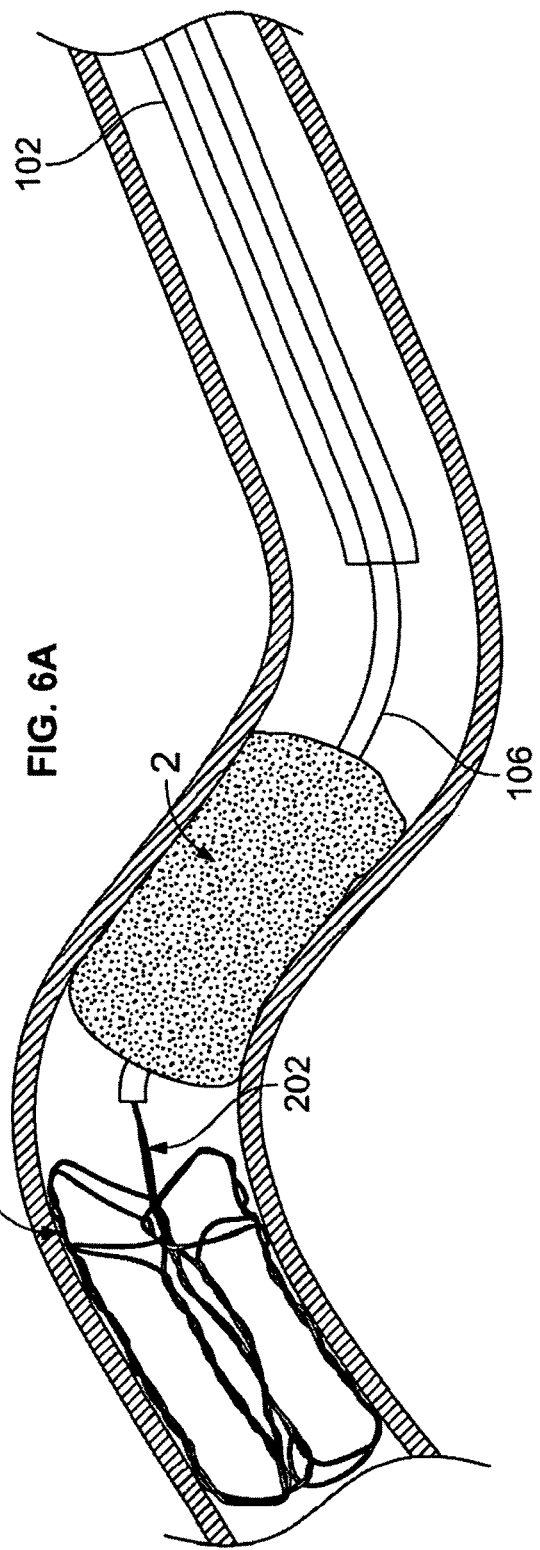

FIG. 6B illustrates deployment of a capturing portion 226 and main bundle 202 of the device 200 from within the microcatheter 102 distal to the obstruction 2. Accordingly, in most variations, the capturing portion 226 is designed to compress within the catheter 102 and expand upon deployment. Alternatively, the device may be actuated to assume the desired shape (e.g., upon reaching a transition temperature where one or more wires comprise a shape memory alloy).

FIG. 6C shows withdrawal of the microcatheter 102 to the proximal side 3 of the obstruction 2 and deployment of a proximal capturing portion 260 (in alternate variations, a proximal foot can be used or the capturing portion 226 alone can be used). Again, the catheter 102 can be exchanged for a catheter 102 having a proximal capturing portion 260. Alternatively, and as shown in the accompanying figures, the proximal capturing portion 260 can be affixed to a delivery sheath 106 that is fed through the microcatheter 102.

As also shown in the figure, the main bundle 202 and capturing portions become misaligned due to the tortuosity of the anatomy. However, because the capturing portions 226 and 260 are able to pivot or articulate relative to the main bundle 202 and catheter 102 or sheath 106, the open ends are able to remain against the lumen wall. In conventional devices where the open end is attached to either a wire or catheter, when the wire or catheter bends in the anatomy, the forces exerted on the open ends deform or distort the end to assume a reduced profile. Accordingly, the physician may have difficulty in removing an obstruction if the profile of the open end becomes reduced in size. Closing of the open end can also result in vascular damage if the physician applies too much force in translating the device.

Figure 6E:
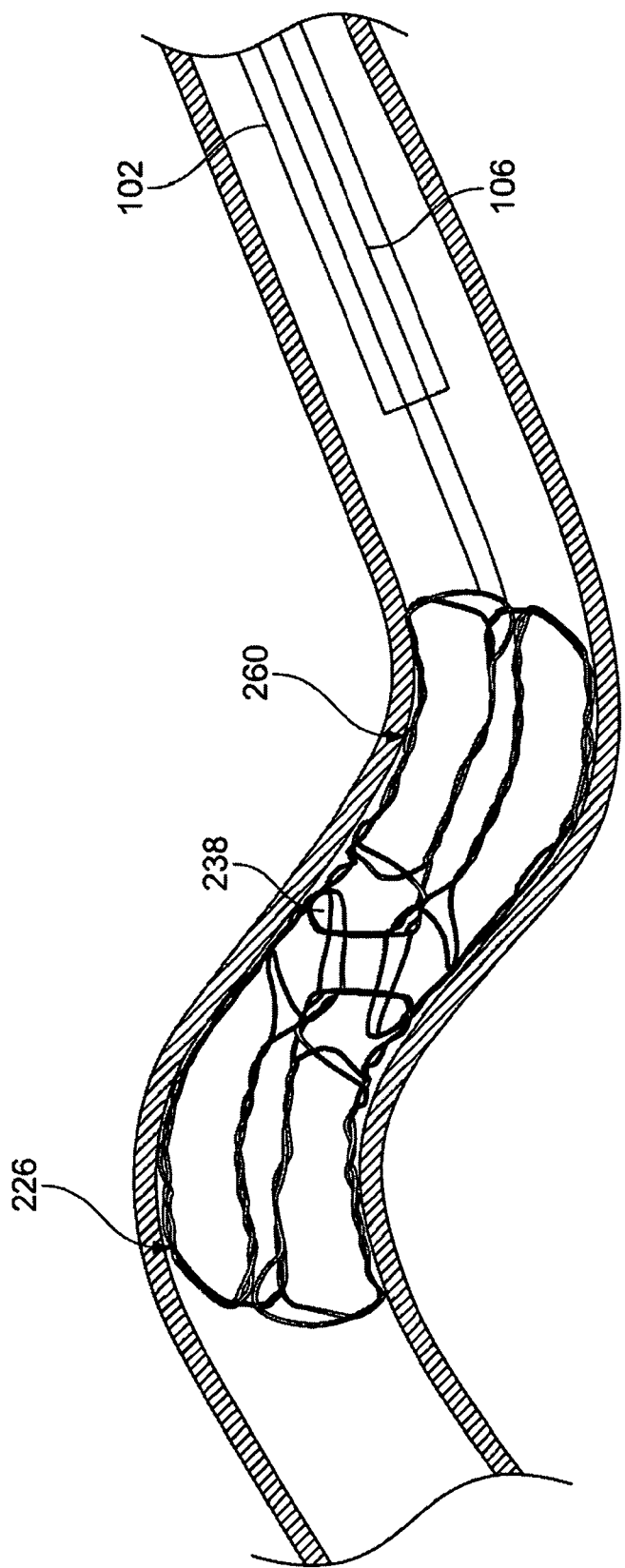

FIG. 6D shows movement of the capturing portions 226 and 260 adjacent to the obstruction 2. The proximal capturing portion 260 can remain stationary or may be advanced relative to the distal capturing portion 226. Regardless, the physician is able to ensnare the obstruction 2 within the cavities defined by the capturing portions 226 and 260. FIG. 6E illustrates the system as the two capturing portions are drawn together. For purposes of clarity, the obstruction is not shown. Upon sufficient advancement of the capturing portion 226 and proximal capturing portion 260 relative to one-another, flanges 238 on the respective open ends can interlock. This feature provides added safety in removing the device as the obstruction is encapsulated between the two nested portions.

Figure 6F:
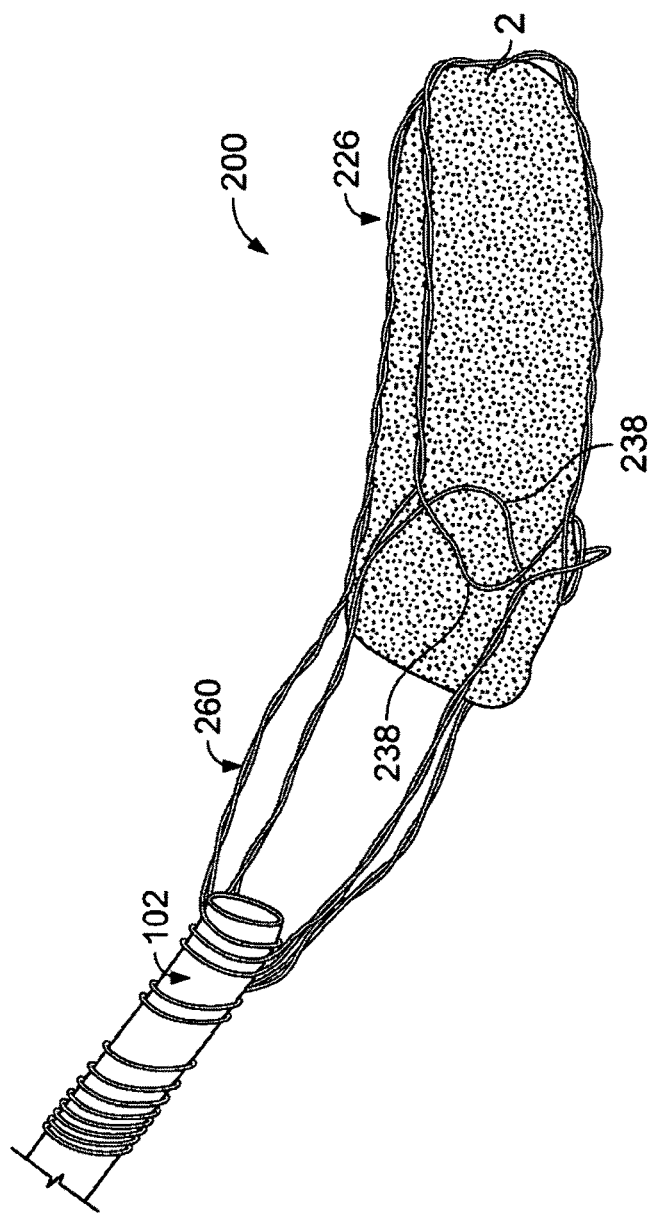
FIG. 6F illustrates a device after securing an obstruction between proximal and distal capturing sections.

FIG. 6F illustrates a device 200 after securing an obstruction between a proximal 260 and distal 226 capturing sections. As shown, the captured obstruction 2 is held between capturing portions 226 and 260 where the flanges 238 nest within one-another to "lock" the capturing portions together. In some variations of the device, one of the capturing portions can be undersized relative to the other. This configuration allows for the undersized capturing portion to become further compressed as the devices are pulled together. The compression of the capturing surface then serves to further compress the obstruction 2 captured within the device.

Figure 7A:
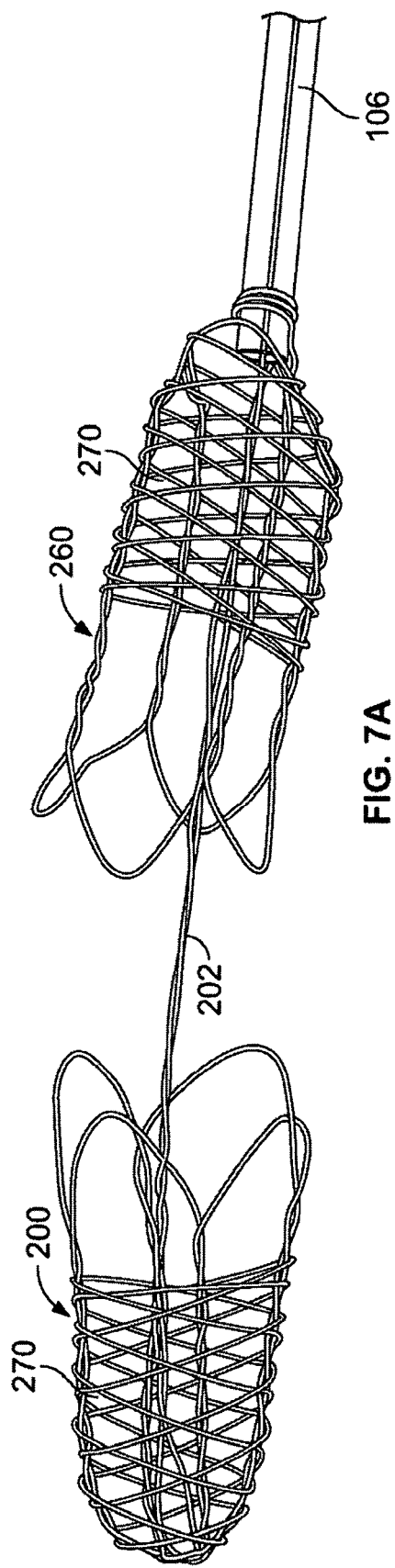
Figure 8B:
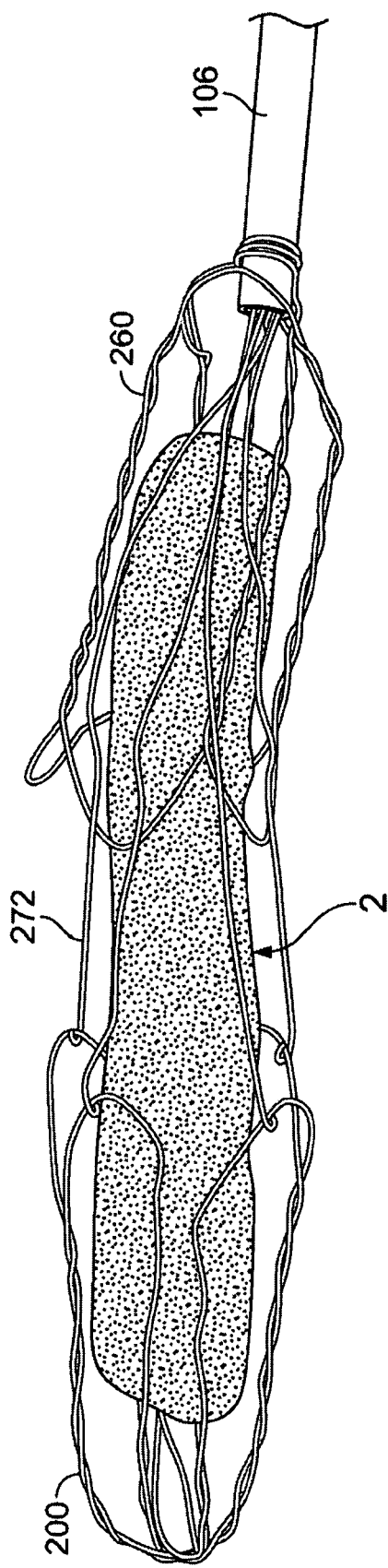

FIGS. 7A to 7B illustrate coverings 270. Although the coverings are located on both capturing portions 200 and 260, only one or more capturing portions can include coverings 270. The covering 270 can include a strand wrapped or woven about the section, a polymer film, or a dipped polymer coating such as silicone, urethane, etc. The coating on either capturing portion can be solid or porous. In the latter case, blood can continue to flow through the coating. In one variation, the proximal capturing portion 260 could employ a solid covering 270 while the distal capturing portion 200 could include a porous covering 270. In such a case, blood or other fluid flow could be temporarily halted by the presence of the solid covering 270 to assist in removal of the obstruction FIGS. 8A to 8B illustrate a system with a distal 200 and proximal 206 capturing portions with an additional set of fibers 272 extending along the inside of portion 200 and along a main bundle or leading wire 202. As the device ensnares an obstruction 2 the fibers are tensioned so that they surround the clot 2 within the capturing portions 200 and 260, as shown in FIG. 8B. In addition, the proximal capturing portion 260 and/or delivery sheath 106 can be rotated relative to the distal capturing portion 200 to twist the fibers 272 allowing improved capture of the obstruction 2.

Figure 9:
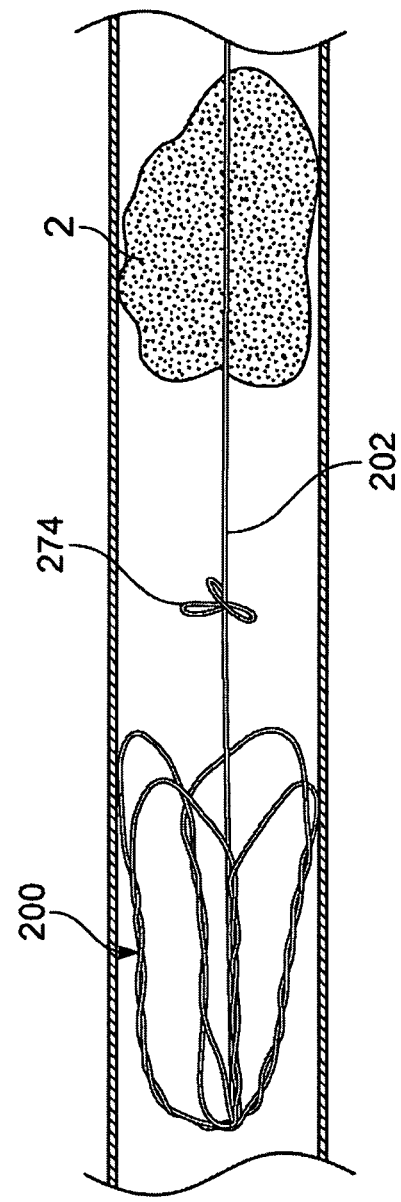
FIG. 9 illustrates a main bundle as including an increased surface area or medial foot that is used to dislodge or loosen the obstruction from a wall of the body passage.

FIG. 9 illustrates another variation of the system where the main bundle 202 includes a medial foot 274. The construction of the medial foot 274 can be similar to that of the proximal foot discussed above (e.g., wires looped into a petal configuration.) However, the medial foot includes a surface area or diameter larger than a diameter of the main bundle. In any case, the increased surface area of the medial foot 274 provides an increased resistance to the obstruction 2 as the distal capturing portion 200 and main bundle 202 are pulled in a proximal direction towards an obstruction 2. The medial foot 274 engages the obstruction 2 to partially displace or loosen the obstruction from the walls of the body passage. The medial foot 274 can be slidably located on the main bundle such that after a threshold force, the medial foot moves within the distal capturing portion 200. The main bundle 202 can include any number of medial feet 274.

Although the illustrated variation shown above comprise open-ended, circular, looped or partial loop shape cross sectional areas, variations of the capturing portions can include any number of shapes. For example, such a shape can include a circle, an arcuate shape, a partial circular shape, a loop, an oval, a square, a rectangle, a polygon, an overlapping loop, a pair of semi-circles, etc.) The various shapes may be heat set to be either self-expanding (i.e., superelastic) or the use of shape memory alloys can allow for the device to assume the particular shape upon reaching a desired transition temperature.

The exemplary shapes discussed above permit the shaped section to adjust in diameter in response to placement in varying diameters of body lumens. It is noted that a device may have different shaped sections on different ends of the device.

While many different shapes are contemplated to be within the scope of this disclosure, the shapes will depend upon the ultimate application of the device. As noted herein, the illustrated examples have particular applicability in retrieving obstructions from the vasculature. Accordingly, for these applications the shaped sections should form a shape so that they can expand against a vessel wall without causing trauma to the vessel. For example, upon release from the catheter, the shaped section can assume their resting shape and expand within the vessel. The resting shape can be constructed to have a size slightly greater than that of the vessel. Sizing the device relative to the target vessel may assist in placing the parts of the device against a vessel.

In an additional aspect, the shaped sections may be designed to have an unconstrained shape that is larger than the intended target vessel or simply different than a cross sectional profile of the intended vessel (i.e., not circular or tubular, but e.g., linear or other different shape). In such an example, as the shaped section is released from the delivery catheter, the shape section attempts to return to the unconstrained shape. In those variations where the unconstrained shape is different from the circular profile of the vessel, the leading wire assumes a shape that accommodates the vessel but is more rigid and stable since its unconstrained shape is entirely different from that of the vessel. In other words, the shaped section continually exerts an outward force on the vessel.

In yet another aspect, the shaped sections shown herein may not necessarily lie in the same plane. Instead, they can be axially spaced by an offset. One benefit of constructing the device to have non-planar shaped section is that the configuration might allow for delivery of the device through a smaller microcatheter because the shaped sections do not interfere with one another when collapsed to fit within the microcatheter.

Another aspect applicable to all variations of the devices is to configure the devices (whether the traversing filament or the surrounding portion) for better adherence to the obstruction. One such mode includes the use of coatings that bond to certain clots (or other materials causing the obstruction.) For example, the wires may be coated with a hydrogel or adhesive that bonds to a thrombus. Accordingly, as the device secures about a clot, the combination of the additive and the mechanical structure of the device may improve the effectiveness of the device in removing the obstruction. Coatings may also be combined with the capturing portions or catheter to improve the ability of the device to encapsulate and remove the obstruction (e.g., a hydrophilic coating).

Such improvements may also be mechanical or structural. Any portion of the capturing portion can have hooks, fibers, or barbs 154 (see e.g., FIG. 2J) that grip into the obstruction as the device surrounds the obstruction. The hooks, fibers, or barbs 154 can be incorporated into any portion of the device. However, it will be important that such features do not hinder the ability of the practitioner to remove the device from the body.

In addition to additives, the device can be coupled to an RF or other power source (such as 14 or 16 in FIG. 1A), to allow current, ultrasound or RF energy to transmit through the device and induce clotting or cause additional coagulation of a clot or other the obstruction.

The methods described herein may also include treating the obstruction prior to attempting to remove the obstruction. Such a treatment can include applying a chemical or pharmaceutical agent with the goal of making the occlusion shrink or to make it more rigid for easier removal. Such agents include, but are not limited to chemotherapy drugs, or solutions, a mild formalin, or aldehyde solution.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

It is important to note that where possible, aspects of the various described embodiments, or the embodiments themselves can be combined. Where such combinations are intended to be within the scope of this disclosure.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

We claim:

1. A medical device for removing an obstruction from a blood vessel, the medical device comprising:
   a first capturing portion having a first distal end, a first proximal end, and a first capturing surface extending between the first distal end and the first proximal end, wherein the first distal end defines a first opening, and wherein the first distal end includes a plurality of first flanges spaced around the first opening, each first flange including one or more wires extending continuously along a peripheral edge of the respective first flange;
   a second capturing portion having a second distal end, a second proximal end, and a second capturing surface extending between the second distal end and the second proximal end, wherein the second proximal end defines a second opening, and wherein the second proximal end includes a plurality of second flanges, each second flange including one or more wires extending continuously along a peripheral edge of the respective second flange; and
   a connecting portion formed from a plurality of wires that extend at least partially through the first and second capturing portions, wherein at least some of the plurality of wires of the connecting portion diverge from each other within the second capturing portion and return to converge together with the connecting portion, wherein the connecting portion is configured to be coupled to an elongate delivery member.

2. The medical device of claim 1, wherein the first opening of the first capturing portion faces the second opening of the second capturing portion.

3. The medical device of claim 1, wherein the first capturing portion is located proximal to the second capturing portion.

4. The medical device of claim 1, wherein a side of the first capturing surface is open.

5. The medical device of claim 1, wherein a side of the second capturing surface is open.

6. The medical device of claim 1, wherein the first capturing surface circumferentially surrounds the connecting portion.

7. The medical device of claim 1, wherein the second capturing surface circumferentially surrounds the connecting portion.

8. The medical device of claim 1, wherein the second capturing portion is coupled to a distal end of the connecting portion.

9. The medical device of claim 1, wherein the first capturing portion has a different shape than the second capturing portion.

10. The medical device of claim 1, wherein the first capturing portion, the second capturing portion, and the connecting portion are self-expandable.

11. The medical device of claim 1, wherein the second capturing portion and the connecting portion are formed from the plurality of wires.

12. A medical device for removing an obstruction from a blood vessel, the medical device comprising:
    a first wire structure having a first distal end, a first proximal end, and a first capturing surface extending between the first distal end and the first proximal end, the first capturing surface defining an axially extending first cavity, wherein the first distal end includes a plurality of first petals oriented in a distal direction, each first petal including one or more wires extending continuously along an edge of the respective first petal;
    a second wire structure having a second distal end, a second proximal end, and a second capturing surface extending between the second distal end and the second proximal end, the second capturing surface defining an axially extending second cavity, wherein the second proximal end includes a plurality of second petals oriented in a proximal direction, each second petal including one or more wires extending continuously along an edge of the respective second petal; and
    a connecting structure formed from a plurality of wires that extend at least partially through the first and second wire structures, wherein at least some of the plurality of wires of the connecting structure diverge from each other within the second wire structure and return to converge together with the connecting structure, wherein the connecting structure is configured to be coupled to an elongate delivery member.

13. The medical device of claim 12, wherein the first wire structure is located proximal to the second wire structure.

14. The medical device of claim 12, wherein the first capturing surface includes one or more openings.

15. The medical device of claim 12, wherein the second capturing surface includes one or more openings.

16. The medical device of claim 12, wherein the first capturing surface circumferentially surrounds the connecting structure.

17. The medical device of claim 12, wherein the second capturing surface circumferentially surrounds the connecting structure.

18. The medical device of claim 12, wherein the second wire structure is coupled to a distal end of the connecting structure.

19. The medical device of claim 12, wherein the first wire structure has a different shape than the second wire structure.

20. The medical device of claim 12, wherein the first wire structure, the second wire structure, and the connecting structure are self-expandable.

21. The medical device of claim 12, wherein the second wire structure and the connecting structure are formed from the plurality of wires.

* * * * *